US012721995B2

(12) United States Patent
McNutt

(10) Patent No.: US 12,721,995 B2
(45) Date of Patent: Sep. 1, 2026

(54) METHOD FOR INCREASING WEIGHT-LOSS DUE TO EXERCISE

(71) Applicant: LF Bolt Corp., Costa Mesa, CA (US)

(72) Inventor: Colleen McNutt, Costa Mesa, CA (US)

(73) Assignee: LF Bolt Corp., Costa Mesa, CA (US)

( * ) Notice: Subject to any disclaimer, the term of this patent is extended or adjusted under 35 U.S.C. 154(b) by 92 days.

(21) Appl. No.: 18/481,225

(22) Filed: Oct. 4, 2023

(65) Prior Publication Data

US 2024/0293664 A1 Sep. 5, 2024

Related U.S. Application Data

(60) Provisional application No. 63/413,593, filed on Oct. 5, 2022.

(51) Int. Cl.
*A61N 1/04* (2006.01)
*A61N 1/36* (2006.01)
*G16H 20/30* (2018.01)

(52) U.S. Cl.
CPC ......... *A61N 1/0452* (2013.01); *A61N 1/0476* (2013.01); *A61N 1/0484* (2013.01); *A61N 1/36031* (2017.08); *A61N 1/36034* (2017.08); *G16H 20/30* (2018.01)

(58) Field of Classification Search
CPC ............................ A61N 1/0452; A61N 1/0484
See application file for complete search history.

(56) References Cited

U.S. PATENT DOCUMENTS

| | | | | |
|---|---|---|---|---|
| 7,551,967 | B1 | 6/2009 | Karicherla et al. | |
| 11,986,652 | B1 | 5/2024 | Ritzen et al. | |
| 2005/0004436 | A1* | 1/2005 | Nissila | A61B 5/02438 600/595 |
| 2005/0015118 | A1 | 1/2005 | Davis et al. | |
| 2007/0179534 | A1* | 8/2007 | Firlik | A61N 1/361 604/503 |
| 2008/0319514 | A1 | 12/2008 | Shi et al. | |
| 2016/0058335 | A1 | 3/2016 | Ashby | |
| 2016/0114160 | A1* | 4/2016 | Scott | A61N 1/36003 607/46 |
| 2016/0213320 | A1 | 7/2016 | Shabah | |
| 2017/0056644 | A1 | 3/2017 | Chahine et al. | |
| 2017/0164832 | A1 | 6/2017 | Kalb et al. | |
| 2017/0224985 | A1 | 8/2017 | Debur et al. | |
| 2018/0036531 | A1 | 2/2018 | Schwarz et al. | |
| 2018/0140901 | A1* | 5/2018 | Wiebe | A61B 5/486 |
| 2019/0247650 | A1 | 8/2019 | Tran | |

(Continued)

FOREIGN PATENT DOCUMENTS

| | | |
|---|---|---|
| CN | 112426624 A | 3/2021 |
| KR | 20130062858 A | 6/2013 |

(Continued)

OTHER PUBLICATIONS

McNutt; U.S. Appl. No. 18/730,299 entitled "Electrical muscle stimulation apparatus and methods," filed Jul. 18, 2024.

(Continued)

*Primary Examiner* — William J Levicky
(74) *Attorney, Agent, or Firm* — Shay Glenn LLP

(57) ABSTRACT

Described herein are therapeutic electrical muscle stimulation (EMS) apparatuses for the increasing weight loss alone or in combination with one or more physical exercises.

20 Claims, 8 Drawing Sheets

(56) References Cited

U.S. PATENT DOCUMENTS

| | | | |
|---|---|---|---|
| 2020/0188653 | A1 | 6/2020 | Dernebo et al. |
| 2020/0197689 | A1 | 6/2020 | Dernebo et al. |
| 2020/0405218 | A1 | 12/2020 | Avila et al. |
| 2020/0406119 | A1* | 12/2020 | Woltermann ........ A61N 1/0452 |
| 2021/0016087 | A1 | 1/2021 | Shahriari et al. |
| 2021/0084999 | A1 | 3/2021 | Matsuura et al. |
| 2025/0325800 | A1 | 10/2025 | McNutt |
| 2025/0381398 | A1 | 12/2025 | McNutt |
| 2026/0000890 | A1 | 1/2026 | McNutt |

FOREIGN PATENT DOCUMENTS

| | | | |
|---|---|---|---|
| KR | 101775506 | B1 | 9/2017 |
| WO | WO2007/138598 | A2 | 12/2007 |
| WO | WO2008/062395 | A1 | 5/2008 |
| WO | WO2022/061250 | A2 | 3/2022 |
| WO | WO2023/230637 | A2 | 11/2023 |
| WO | WO2023/250502 | A2 | 12/2023 |
| WO | WO2024/006755 | A2 | 1/2024 |

OTHER PUBLICATIONS

McNutt et al; U.S. Appl. No. 18/479,787 entitled "Therapeutic electrical muscle stimulation apparatus and method of improving medical procedure outcomes," filed Oct. 2, 2023.

Feng; Sensor Suits for Human Motion Detection; Report No. UCI-CEE-03-F03; California Univ. Irvine; 2006; 19 pages; retrieved from the internet (https://apps.dtic.mil/sti/pdfs/ADA444285.pdf).

Liegnell et al.; Validity of ultrasonography-derived predictions for estimating skeletal muscle volume: a systematic literature review; BMC medical imaging: 21(1); 106; 11 pages; Jul. 5, 2021.

Nakanishi et al.; Monitoring of muscle mass in critically ill patients: comparison of ultrasound and two bioelectrical impedance analysis devices; Journal of intensive care; 7(1); 61; 8 pages; Dec. 16, 2019.

* cited by examiner

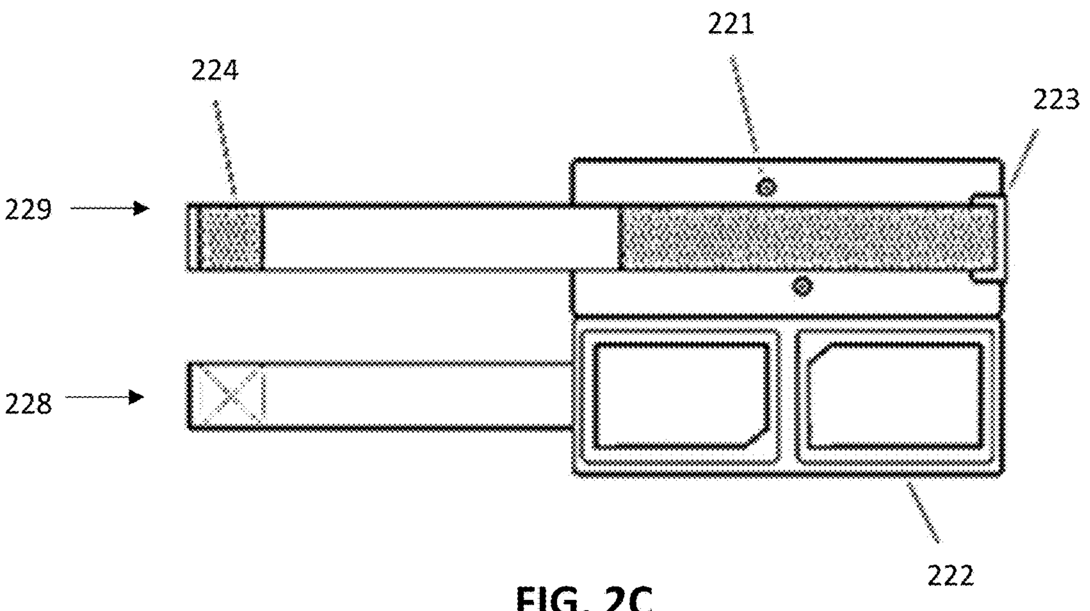
FIG. 2C
FIG. 3A
FIG. 3B

FIG. 4A
FIG. 4B
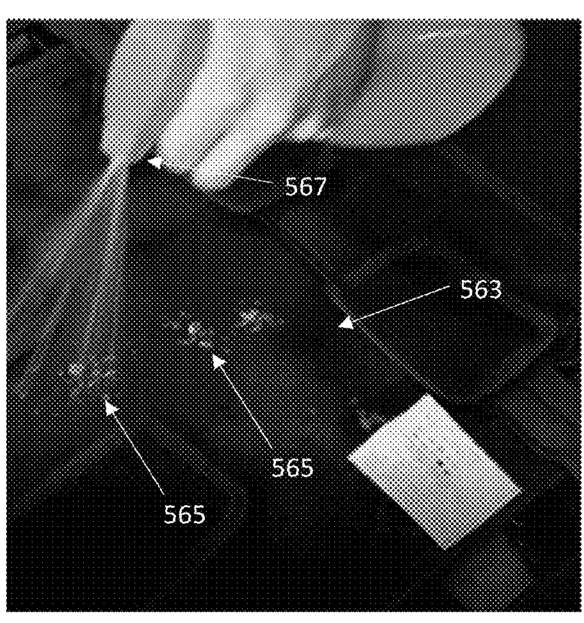
FIG. 5

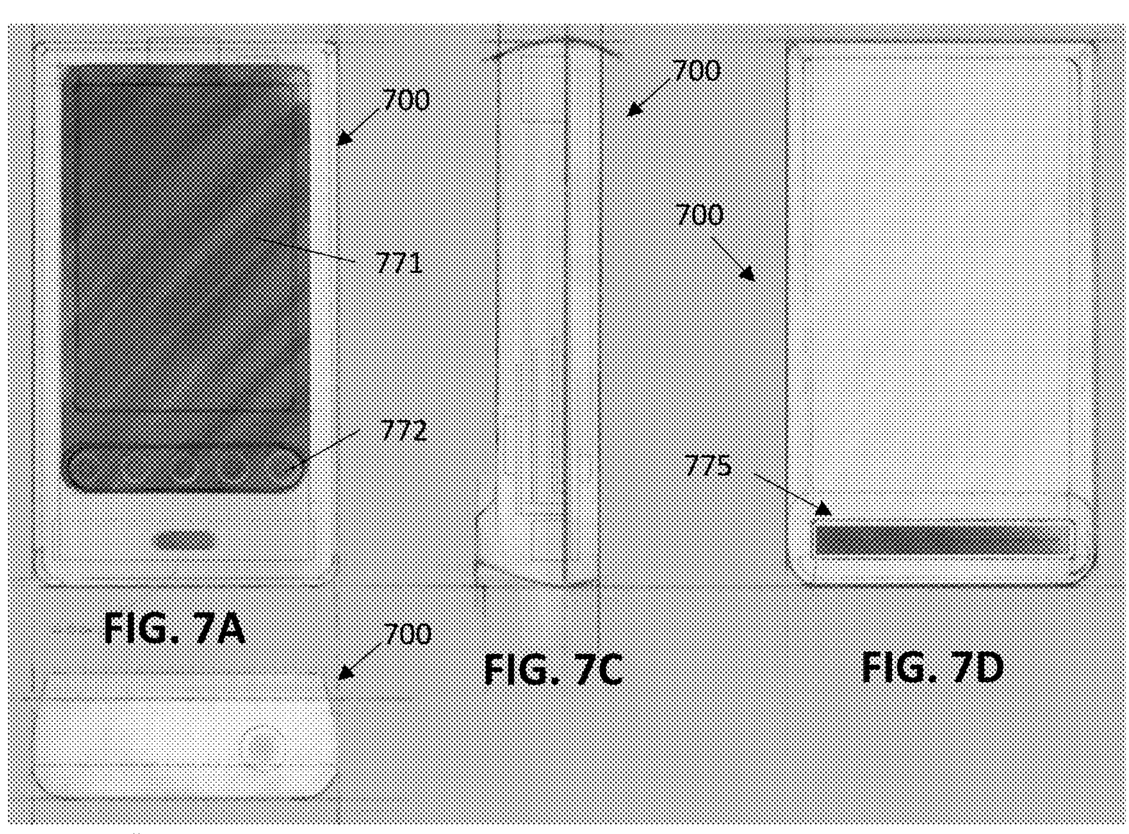
FIG. 7A
FIG. 7B
FIG. 7C
FIG. 7D
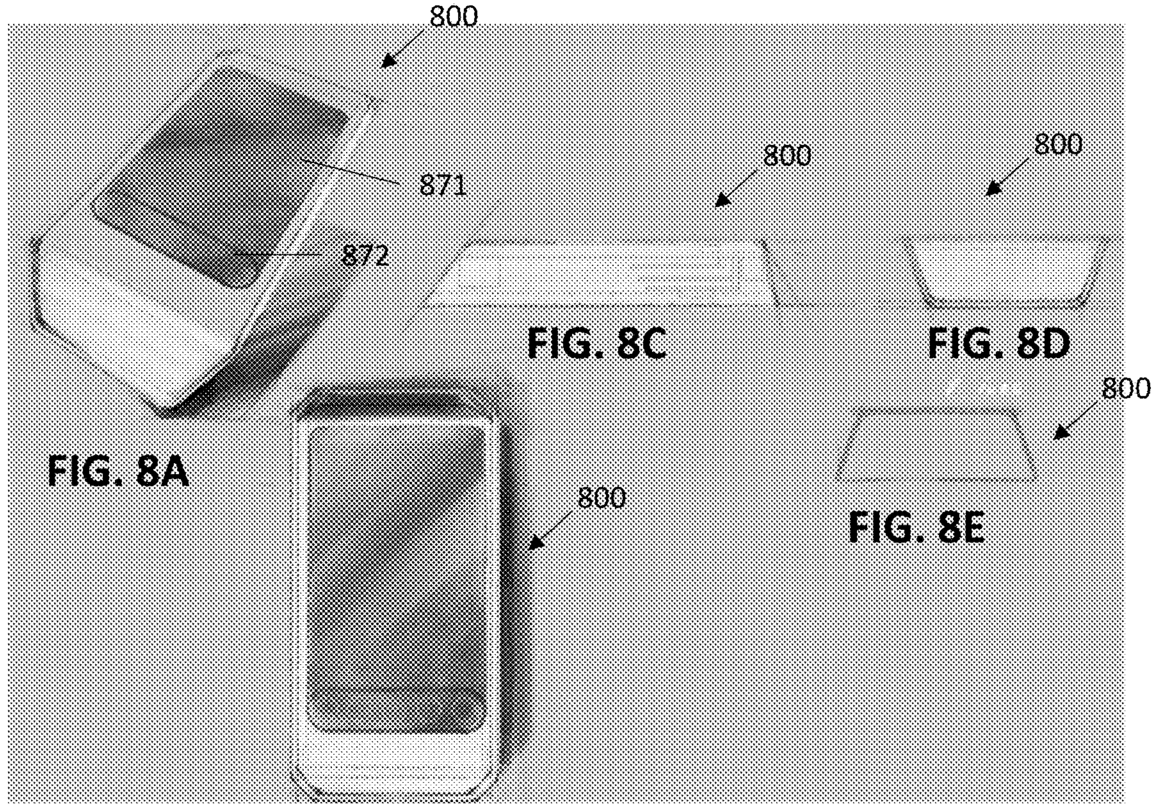
FIG. 8A
FIG. 8B
FIG. 8C
FIG. 8D
FIG. 8E

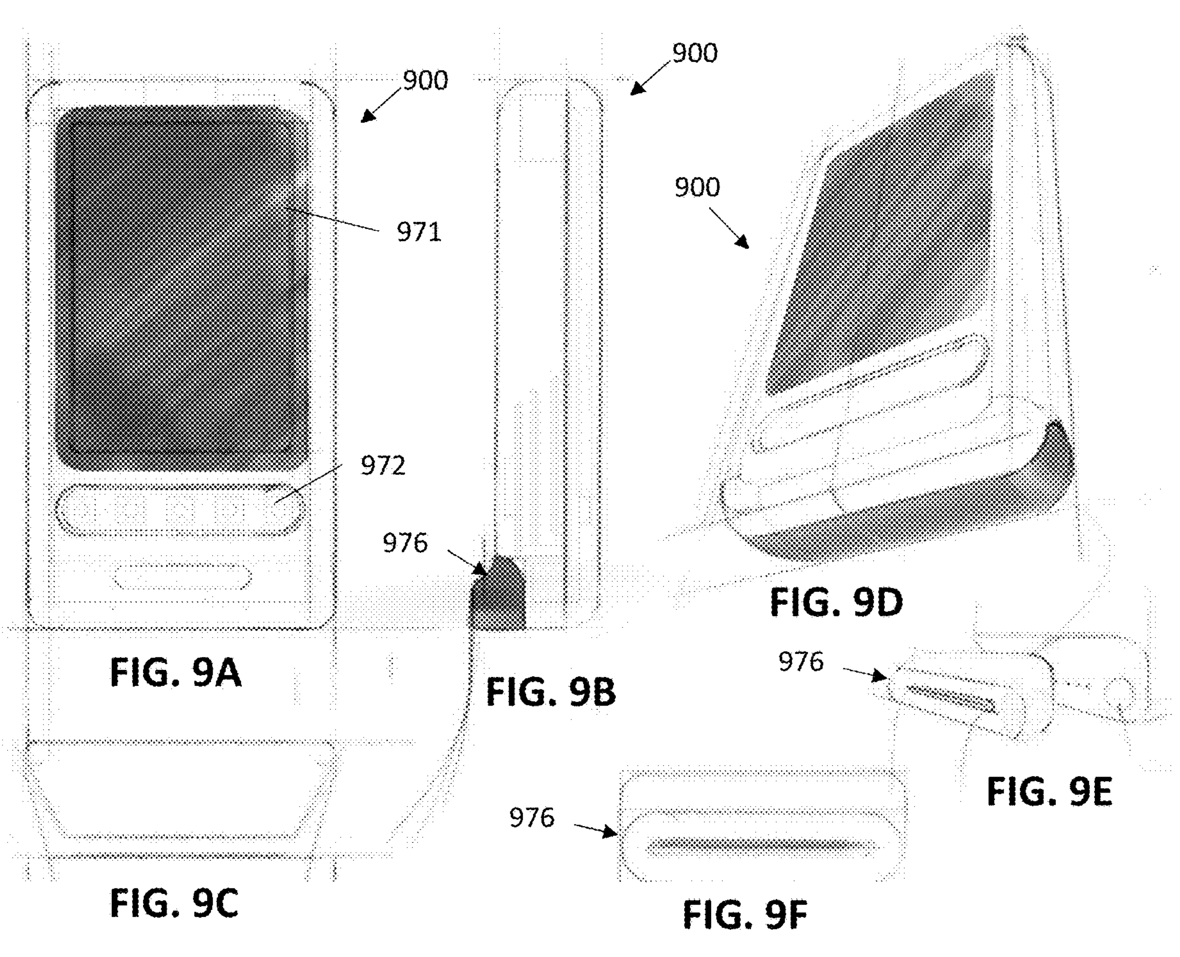
FIG. 9A
FIG. 9B
FIG. 9C
FIG. 9D
FIG. 9E
FIG. 9F
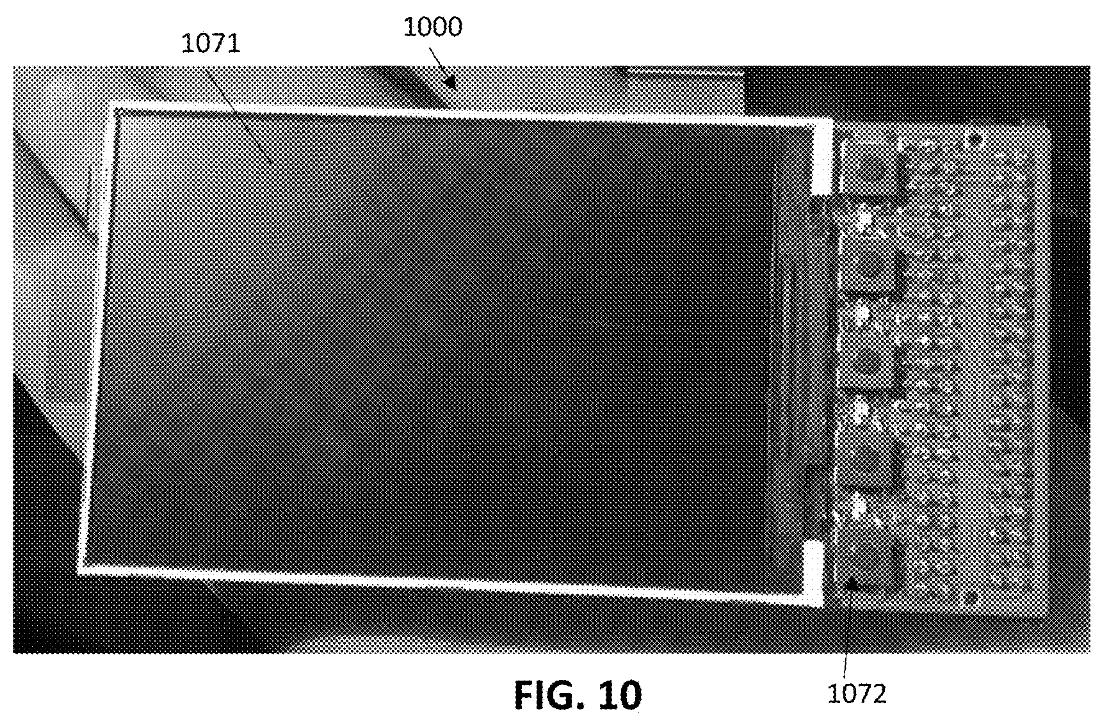
FIG. 10

METHOD FOR INCREASING WEIGHT-LOSS DUE TO EXERCISE

CLAIM OF PRIORITY

This application claims the benefit of U.S. Provisional Patent Application No. 63/413,593, filed Oct. 5, 2022, titled "THERAPEUTIC ELECTRICAL MUSCLE STIMULATION APPARATUS AND METHOD OF TREATMENT," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Accumulation of excess body fat (e.g., adiposity) is a major contributor to several different diseases from diabetes and cancer to heart disease and neurodegenerative disorders. Studies suggest a rising incidence of obesity in recent years approaching 50% of the adult population in the United States.

Adiposity can be a multifactorial condition attributable to genetic and/or lifestyle factors promoting the development and retention of adipose tissue throughout the body. A healthy diet and exercise are universally understood examples of lifestyle activities to prevent or decrease accumulated fat. However, compliance with healthy habits is a significant challenge against effective weight loss and management. Additionally, lifestyle changes may fail to address associated underlying genetic factors.

Currently, medications are available including pharmaceuticals and over-the-counter supplements attempt to promote or support metabolic processes involved in reducing fat. As with most medications, these are associated with side effects including potentially life-threatening risks. Current alternatives to fat-loss medications include mechanical interventions ranging from cryogenic techniques to invasive surgical procedures.

Electrical Muscle Stimulation (EMS) is generally understood as a therapeutic option for the treatment of certain diseases and conditions via electrically stimulating one or more muscles. Considering various traditional exercise methodologies, targeted muscle contraction is one of the main objectives of physical exercise to address obesity by beneficially impacting metabolic processes. While EMS may provide predictable stimulation, current devices and methods fail to accommodate user-specific feedback and optimized stimulation protocols. In addition to the lack of a tailored capacity for effective stimulation, lack of user compliance, and an inability to combine EMS therapy with physical exercise highlights some of the deficiencies of existing EMS systems Even where EMS may be adaptable based on uploaded treatment protocols, there is still a failure to appreciate the individuality, personalization, and rapid response needed to improve the quality of life for these patients. In addition, EMS is generally only available for patients currently diagnosed with a disease or condition.

For these reasons, it would be desirable to provide improved methods, systems, and tools for increasing weight loss and treating underlying causes of obesity. It would be particularly desirable to provide a patient-specific system including devices that promote treatment compliance and efficacy. At least some of these objectives will be met by the various embodiments that follow.

SUMMARY OF THE DISCLOSURE

Described herein are apparatuses (including EMS suits, user interfaces, and control systems, etc.), which may include hardware, software and/or firmware, for electrical muscle stimulation (EMS) systems that may provide electrical stimulation for increased weight-loss alone or in combination with physical exercise. In general, the apparatuses and methods described herein may be used as part of a therapeutic or non-therapeutic procedure. For example, these methods and apparatuses may be part of an exercise or fitness (including weight loss) regime. However, the methods and apparatuses described herein may also or alternatively be used as part of a therapy, such as in particular for physiotherapy and/or for treatment of a condition or a disease.

In general, a method for increasing weight-loss due to exercise can comprise positioning an electrical muscle stimulation (EMS) suit apparatus on a patient. The EMS suit apparatus can have one or more electrodes locatable in direct contact with the patient's skin. Stimulation can then be supplied to one or more target muscle groups, via EMS power from the one or more electrodes. Confirmation can be provided to the patient regarding use of the target muscle group based on the patient movement data.

In some examples, the one or more one or more electrodes can be disposed on an inner surface of the EMS suit apparatus. The positioning of the EMS suit can comprise wearing, by the patient, the EMS suit apparatus. The EMS suit apparatus can include an upper torso portion, a lower portion, or a combination thereof.

In some examples, the target muscle group may include quadriceps, hamstrings, glutes, abdominals, chest, lower back, mid back, upper back (trapezius), biceps and triceps, calves, or a combination thereof.

In some examples, the method may include receiving patient biometric data from one or more sensors in operable communication with the EMS suit apparatus. The patient can perform a first exercise. In some examples, stimulation is supplied to the one or more target muscle groups prior to the first exercise. In some examples, the stimulation is supplied to the one or more target muscle groups after the first exercise. In some examples, the stimulation is supplied to the one or more target muscle groups during the first exercise.

In some examples, the method comprises the patient performing a subsequent exercise. The EMS apparatus may verify, by the controller, performance of the first exercise. In some examples, the stimulation is supplied to the one or more target muscle groups prior to the subsequent exercise. In some examples, the stimulation is supplied to the one or more target muscle groups after the subsequent exercise. In some examples, the stimulation is supplied to the one or more target muscle groups during the subsequent exercise.

In some examples, the EMS power may be based on an initial baseline level, a user provided input, a power level provided by clinician, or a combination thereof. In some examples, the EMS power may be adjustable based on biometric data acquired by one or more sensors in operable communication with the EMS suit apparatus.

The confirmation may include a visual indication, a verbal confirmation, a haptic indication, or a combination thereof.

The method may also include establishing, by a controller, a stimulation regime based on patient biometric data. The stimulation regime can be adjustable by the controller.

In some examples, the method may include, prior to providing EMS power to the one or more EMS electrodes, determining movement of the target muscle group; and providing EMS power in response to determining movement of the target muscle group.

In some examples, the method may include determining a weight loss of the patient with respect to a predetermined time period; and providing, to the patient, revised exercises to perform for the target muscle group, wherein the revised exercises are based on the determined weight loss of the patient. The stimulation can be supplied to the one or more target muscle groups before an exercise, during an exercise, after an exercise, or a combination thereof.

In general, an electrical muscle stimulation (EMS) apparatus, for increasing weight-loss due to exercise, may comprise a first garment configured to be worn on an upper torso of a patient. The first garment may comprise one or more electrical muscle stimulation (EMS) electrodes configured to make direct contact with a patient's skin proximate to a target muscle group. One or more sensors can be configured to acquire patient biometric data, and a controller coupled to the sensor may be configured to provide EMS power to the one or more EMS electrodes; and provide a confirmation of use of the target muscle group based on the patient movement data.

In some examples, the EMS apparatus may comprise a second garment comprising one or more electrodes in operable communication with the patient's skin, the second garment configured to be worn over a lower portion of the patient including the patient's legs.

The one or more sensors can be configured to provide patient biometric data before an exercise, during an exercise, after an exercise or a combination thereof. Examples of the target muscle group may include quadriceps, hamstrings, glutes, abdominals, chest, lower back, mid back, upper back (trapezius), biceps and triceps, calves, or a combination thereof. The one or more sensors may also comprise at least one accelerometer configured to provide patient movement data.

In some examples, the controller can be further configured to display a first exercise for the patient to perform with the target muscle group. The controller can be further configured to confirm that the use of the target muscle group is within a predetermined level. In some examples, the controller can be further configured to display a second exercise for the patient to perform after verification of performance of the first exercise. In some examples, the controller can be configured to provide EMS power based on an initial baseline level, a user provided input, a power level provided by clinician, or a combination thereof. The EMS power can be adjustable based on the acquired biometric data from the one or more sensors.

In some examples, the controller can be configured to provide confirmation of an exercise performance via a visual indication, a verbal confirmation, a haptic indication, or a combination thereof displayable on the controller.

In some examples, the patient movement data may indicate use of the target muscle group while EMS power is concurrently supplied to the one or more EMS electrodes.

In some examples, the controller can be further configured to determine movement of the target muscle group prior to providing EMS power to the one or more EMS electrodes; and provide power to the EMS electrodes in response to a determination of movement of the target muscle group. In some examples, the controller can be further configured to determine a weight loss of the patient with respect to a predetermined time period; and provide revised exercises to perform for the target muscle group, wherein the revised exercises are based on the determined weight loss of the patient. The controller can be configured to display the revised exercises. The the controller can be configured to direct the EMS power to the target muscle group, one or more non-target muscle groups, or a combination thereof.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 2A-2C show an example of parts of an EMS apparatus.

FIGS. 3A-3B illustrate examples of EMS apparatuses (e.g., EMS suits) worn on a user.

FIGS. 4A-4B show another example of an EMS apparatus as described herein.

FIG. 5 illustrates hydrating an example of an electrode for an EMS apparatus.

FIGS. 7A-7D illustrate an example of a combined power supply and controller for an EMS apparatus as described herein.

FIGS. 8A-8E illustrate an example of a combined power supply and controller for an EMS apparatus.

FIGS. 9A-9F illustrate an example of a combined power supply and controller for an EMS apparatus.

FIG. 10 illustrates one example of a portion of a combined power supply/controller for an EMS apparatus.

DETAILED DESCRIPTION

Figures 1A, 1B, 1C, 1D, 1E, 1F:
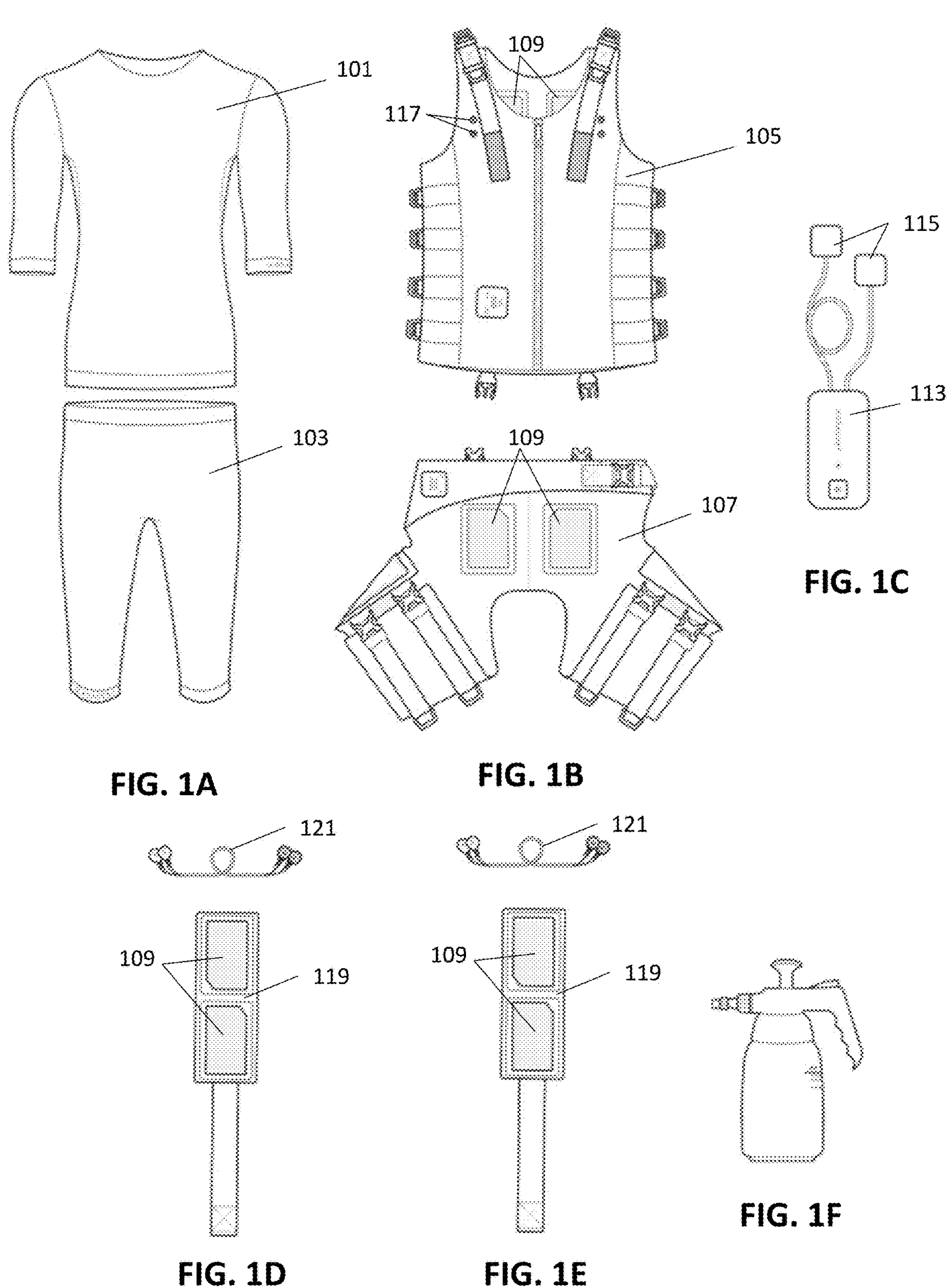
FIGS. 1A-1F show one example of an EMS apparatus as described herein.

Described herein are electrical muscle stimulation (EMS) apparatuses (e.g., devices and systems, including suits, controls, operational protocols, etc.) including a therapeutic system to reduce body fat and increase weight loss. The EMS apparatuses may include a plurality of structural elements adapted to acquire user-specific data that can be interpreted by the EMS apparatus for the development of a stimulation protocol. The stimulation protocol can be configured to maximize an impact of the EMS alone and/or in combination with one or more weight loss interventions (e.g., exercise). The structural elements may include sensors associated with the EMS apparatus and configured to obtain user-specific data before, during and/or after use that may relate to one or more characteristics and/or a composition of one or more tissues of the user (e.g., patient).

A user (e.g., patient) may engage an EMS apparatus alone or in combination with one or more physical activities (e.g., exercise). For examples, a user may engage an EMS apparatus to receive electrical stimulation supplied thereby to increase weight loss alone or in combination with an exercise routine performed before, during, and/or after engaging the EMS apparatus. In some examples, an EMS apparatus described herein may be configured to stimulation contraction of one or more muscles. Muscle contraction via an EMS apparatus (e.g., electrical stimulation) can instigate contraction of different muscles compared to contraction of muscles without the influence of an external structure or xenobiotic. In addition to the potential for contracting different muscles, an EMS apparatus described herein can be configured to supply targeted EMS muscle contraction including targeting muscle contraction with pre-determined stimulation protocol.

An EMS apparatus described herein may be configured to supply electrical stimulation to one or more biological tissues beneficially impacting intracellular processes (e.g., metabolic and mitochondrial activities). For example, the electrical stimulation supplied via an EMS apparatus described herein may increase mitochondrial activity and cellular metabolism. In some examples, the EMS simulation supplied via an EMS apparatus described herein may increase thermogenesis or other cellular processes associated with increase calorie consumption and fat loss.

In some examples, an EMS apparatus described herein can provide electrical stimulation and stimulation protocols resulting in significant changes in biochemical parameters and body composition. The electrical stimulation including the stimulation protocol may be delivered via an EMS apparatus alone or in combination with physical exercise to increase muscle recruitment. For example, physical exercise may be associated with muscle contraction via signals from the user's own central nervous system (CNS). The muscles activated via CNS signaling maybe the same, similar, different, or a combination thereof compared to the muscles activated via electrical stimulation supplied by an EMS apparatus described herein. Accordingly, a combination of physical exercise and electrical stimulation via an EMS apparatus may beneficially increase weight loss (e.g., decrease in adipose tissue). For example, a combination of physical exercise and EMS stimulation (e.g., via an EMS apparatus) may be configured to activate one or more muscle groups in an order, pattern, frequency, intensity, etc. based on a type of muscle fiber, innervation, motor neurons (e.g., alpha motor neurons), etc. or a combination thereof. For example, the CNS of a user may activate smaller alpha motoneurons during physical activity (e.g., exercise) and an EMS apparatus may also activate the smaller alpha motor neurons and/or may activate another type of motor neuron (e.g., larger alpha motor neurons) before, during, and/or after the CNS activation.

Any EMS apparatus, system and/or method described herein may be configured to supply electrical stimulation to anatomy of a user to increase weight loss. In some examples, the electrical stimulation may be supplied based on one or more factors such as, a quantity, composition, location, condition, etc. or a combination thereof adipose tissue of the user. In some examples, the electrical stimulation may be supplied based on one or more factors such as, a quantity, composition, location, condition, etc. or a combination thereof muscle tissue of the user. These factors can be determined by one or more sensors in operable communication with the EMS apparatus and the user. In some examples, the one or more factors that may be interpreted for determination stimulation protocol may be based on data obtained by the EMS apparatus via one or more inputs or databases associated with the user and/or stimulation protocol attributes.

Each of the sensors may be configured to receive or acquire data that may be interpreted by the therapeutic system and used in the development of a stimulation protocol and application of the same via an EMS apparatus described herein. For example, the sensors may detect or acquire biometric data associated with the user. In some examples, one or more sensors of the EMS apparatus may be configured to acquire environmental data, operational data of the EMS system (e.g., EMS apparatus), user-specific data, or a combination thereof.

In some examples, the therapeutic system may include an interface operably connected to the therapeutic system and configured to receive one or more inputs relating to the user. For example, the user interface may receive user input to generate a profile of the user that may adjust parameters of the therapeutic system (e.g., the sensors). In some examples, the interface may be in communication with one or more databases or electronic systems having data generated or established outside of the EMS apparatus, which may be incorporated into the therapeutic system operations. For example, the interface may communication with one or more electronic medical record systems having user-specific information such as medical history, lab test results, examination notes, or other relevant information related to a disease, condition, risk factor thereof, including a quantity, accumulation of, composition of, molecular signatures associated with adipose tissue. The therapeutic system may interpret this remote user-specific information and adjust one or more of the sensors or one or more parameters for the sensors operation to target sensor operation based on the remote user-specific information.

In some examples, the EMS apparatuses may include one or more sensors configured to acquire and/or generate data and information within the apparatus to detect, diagnose, prevent, and/or treat a disease of condition (e.g., a neurological disorder) based on user-specific characteristics. The sensors may utilize various techniques to acquire biological and physiological information (e.g., muscle characteristics) from a user. For example, the sensors may be configured to detect one or more attributes of an accumulation of adipose tissue (e.g., fat) that may be interpreted by the EMS apparatus (e.g., via a therapeutic system) and used in determining, establishing, and/or executing therapeutic stimulation protocols based on the detected attributes. The stimulation treatment protocols may be adapted to a disease, condition, predisposition, real-time status, or other factors known or suspected to be associated with the accumulation of adipose tissue.

In some examples, an EMS apparatus as described herein may include one or more sensors to acquire user-specific biometric data related to adipose tissue (e.g., an accumulation of adipose tissue). For example, one or more sensors may include an ultrasound sensing system to determine thickness, density, geometry, etc. of an accumulation of adipose tissue. The EMS apparatus (e.g., EMS suit) may include one or more ultrasound (e.g., ultrasonic) sensors located or locatable within, on and/or associated with the EMS suit to sufficiently operate and detect user-specific data. Ultrasound system (e.g., an ultrasound sensor) may be configured to sense, determine, evaluate, etc. fat (e.g., subcutaneous adipose layers) within an area or region of the user's anatomy and/or the user's entire body. The detected quantity, composition, and detail of the adipose tissue may include a ratio relative to previous acquired data by the EMS suit and/or a database of established parameters related to adipose tissue of a user-matched (e.g., height, weight, age, sex, etc.).

In some examples, an EMS apparatus may have one or more accelerometer sensors. The accelerometer sensors may be configured to detect a movement of the suit engaged by a user (e.g., patient) and thereby detect the movement, activity, etc. of the user or a region of the user's anatomy. Detection by the sensor may include acquiring data by the sensor that is interpreted by the EMS apparatus (e.g., the therapeutic system). Based on the interpretation and acquired data, the EMS apparatus may provide an alert or notification of the detected movement including the voluntary or involuntary contracting of one or more muscles (e.g., muscle groups). For example, the alert or notification may be a visible indicator or a threshold goal for a movement (e.g., an exercise activity). For example, the user may engage the EMS apparatus and begin an exercise activity. The suit may detect movement via the one or more accelerometer sensors and display or provide an alert to increase, decrease, maintain or a combination thereof, the activity responsible for the detected movement (e.g., an exercise activity). A steady state of movement may include no movement (e.g., sedentary) or movement that is associated with natural or native biomechanical operation of a user's anatomy (e.g., biological tissue such as musculature). The accelerometer sensors may include one or more inertia measuring units (IMUs) configured to detect or acquire user-specific data associated with the inertia of the user's anatomy.

In some examples, the EMS apparatus may supply electrical stimulation via one or more electrodes as described herein. For example, a stimulation protocol may be established based on the sensor data or interpretation of the sensor data including stimulation parameters such as stimulation intensity, duration, anatomic location, sequence, etc. In some examples, the stimulation protocol may be adjustable based on subsequent data acquired by one or more of the sensors associated with the EMS apparatus (e.g., EMS suit). In some examples, the adjustment is dynamic and may increase or decrease or a combination in increase and decrease one or more of the stimulation parameters based on the subsequently acquired data. For example, an initial stimulation protocol may be established based on the detection and/or acquisition of user-specific data and, after a period of time (e.g., period of use) additional data may be acquired that may cause the stimulation protocol to change one or more of the stimulation parameters. In some examples, the stimulation protocol may terminate after a therapeutically effective stimulation has been supplied. In some examples, the stimulation protocol may terminate after a period of stimulation prior to, during, and/or after physical exercise.

In some examples, the EMS apparatus may acquire user-specific data before, during or after initiation of a stimulation protocol and may adjust one or more of the stimulation parameters based data associated with user response to the stimulation and/or the physical exercise. For example, a stimulation protocol may acquire user-specific temperature data, heart rate data, respiration, etc. and determine whether or not to continue the stimulation protocol, adjust the stimulation protocol, or terminate the stimulation protocol.

One or more of the sensors may include a thermal sensor configured to detect biometric data related to the internal and/or external temperature of a user. Body temperature may be a factor of physical activity (e.g., energy exerted during physical activity), thermogenesis, one or more disease states, etc. or a combination thereof. The body temperature data may be used by the EMS system for establishing and/or adjusting a stimulation protocol as well as detecting, predicting, treating, preventing or diagnosing a disease of condition. The thermal sensors (e.g., temperature sensors) may be located or locatable on the EMS apparatus to acquire or detect the temperature of the user via contact, infrared sensing, etc. The data may then be sent to the processing unit for interpretation and analysis according to any of the processes described herein.

One or more of the sensors may be adapted to detect user-specific biometric data associated with respiration. For example, respiration volume, cadence, pulse oxygen levels, etc. may be detected by the one or more respiration sensors. In some examples, the respiration sensors may include sensors associated with the EMS suit that detect a change in volume as the user inhales. For example, resistance sensors positioned throughout the suit may detect a strain on the EMS suit as the user inhales. The quantity of strain detected may be interpreted in one or more algorithms adapted to quantify the volume and rate of respiration. The respiration sensors may also include an optical element configured to detect pulse oxygen through optically sensing a flow of blood through one or more blood vessels associated with the sensor.

In some examples, the respiration sensors may acquire user-specific data associated with a condition affecting respiration (e.g., hyperventilation) and may adjust one or more of the stimulation parameters accordingly. In some examples, the data acquired by the one or more sensors may be over one or more periods of time (e.g., continuous, periodic, etc.) Multiple sensors may provide data that can be aggregated and interpreted by the EMS apparatus to determine the impact of the physical exercise on the user. The stimulation protocol may be adjusted according to the changes resulting from the physical exercise.

One or more of the sensors may include an electromyography sensor configured to detect electrical events associated with muscle function. Electromyography sensors may detect or acquire user-specific data associated with the function of a muscle and may be configured to predict voluntary, involuntary or a combination of involuntary and voluntary muscle function.

Detection of user-generated electrical signaling may provide data related to the incidence or prediction of an impending disease-associated biological activity. For example, the electromyography sensors may detect impulses from the nervous system to one or more biological tissues related to a disease-associated biological activity simultaneously, or prior to the incidence. The data may be interpreted by the processing unit and may be a factor in initiating, adjusting, and/or terminating the stimulation protocol. For example, treatment incorporating electromyography sensor data may provide support for stimulation parameters and supplying of EMS by the one or more electrodes.

In some examples, one or more sensors may be configured to detect, sense, determine, or otherwise evaluate characteristics of one or more muscle groups of the user to optimize the stimulation protocol. For example, muscle characteristics such as density, mass, activity, etc. may relate to pre-determined or anticipated reaction to an electrical stimulation from the EM apparatus. The EMS apparatus may be configured to deliver or supply electrical stimulation having characteristics to activate, trigger, contract, or otherwise illicit a response from one or more muscles. The EMS apparatuses described herein may determine a pattern, region, location, duration, intensity, frequency, etc. of electrical stimulation illicit an optimum response from one or more muscles to maximize the amount of calories burned during the muscle activity. In some examples, the EMS apparatus may be configured to supply an electrical stimulation having certain stimulation parameters directed to targeting specific types of muscle fiber within one or more muscles. For example, muscle fibers may be slow oxidative (SO), fast oxidative (FO) and fast glycolytic (FG). Any EMS apparatus described herein may be configured to stimulation one or more of the muscle fiber types.

In some examples, the user via physical exercise will activate one or more muscle fibers. When the physical exercise is performed in combination with (e.g., prior to, during, and/or after) the EMS stimulation, the EMS apparatus may be configured to stimulate those fibers that are under-stimulated or not stimulated by the user via the physical exercise. For example, the user via their CNS may stimulate FG muscle fibers more than FO or SO fibers and the EMS apparatus may be configured to detect the muscle characteristics stimulated by the CNS and deliver electrical stimulation configured to stimulate the remaining muscle fibers. In some examples, the EMS apparatus may determine via one or more sensors what type of muscle fibers are stimulation by the CNS during physical activity and deliver (e.g., supply electrical stimulation to the same muscle fibers. In some examples, the EMS stimulation may be configured to amplify the CNS stimulation. In some examples, the EMS stimulation may be configured to support or compensate for any deficiency of the CNS stimulation during the physical activity.

Any EMS apparatus described herein may be configured to determine, sense, or otherwise acquire data relating to characteristics of one or more muscles. The muscle characteristics may relate to the form and/or function of one or more muscle groups, muscles, or regions of muscle. One example of a muscle characteristic can be muscle density. The muscle characteristics may be entirely acquired by the sensors. In some examples, elements of a muscle characteristic may be acquired by the sensors and input into one or more algorithms adapted to calculate or quantify a muscle characteristic including the acquired data. In some examples, a quantification of muscle density may relate to a ratio of muscle to non-muscle tissue across or throughout an area of a user's body. In some examples, a quantification of muscle density may relate to a ratio of lean muscle to other tissue across or throughout an area of a user's body. In some examples, a quantification of muscle density may relate to a ratio of muscle tissue (e.g., muscle fiber) concentration within, across or throughout a user's body.

In general, an EMS apparatus may include an EMS suit having one or more sensors coupled or couplable thereto. Sensors may be associated with the EMS suit in a configuration allowing for associated operation of the sensor to acquire data and information. The sensors may be operably connected to the EMS suit and/or associated with one or more elements associated with the EMS suit (e.g., electrical circuitry, electrodes, controller, processor, power supply, etc). Each sensor may operate independently or in combination with one or more other sensors or EMS suit elements to acquire and/or determine user-related attributes (e.g., muscle characteristics) and transmit the user-related attributes to the EMS system associated with the system for stimulation and/or stimulation protocol management.

The EMS apparatuses, as described herein, may include optical sensors configured for measuring user-specific muscle characteristics. Optical sensors may be located or locatable on the EMS suit. The location or disposition of the optical sensors may be based on target areas of the user subject to analysis. Optical sensors may be located on the EMS suit in a position exterior of the user and proximal to a muscle group. For example, the pectoralis major muscles are generally located bilaterally of a sagittal plane and inferior to the clavicle. Optical sensors configured to acquire muscle density of the pectoralis major muscles may, therefore, be correspondingly positioned on the EMS suit at or near the anatomical location of the pectorals muscles. In some examples, the optical sensors may be configured to determine one or more characteristics of any biological tissue. For example, one or more optical sensors in operable communication with the EMS apparatus may be configured to determine a location, concentration, type, density, etc. of fat (e.g., adipose tissue).

Optical sensors may operate based on the transmission of light modified by one or more body tissues (e.g., adipose tissue). Adipose tissue characteristics may be determined or determinable based on the changes in light emitted from the optical sensors. Changes in light may relate to changes or modifications in one or more attributes of the light emitted by the optical sensors. The emitted light is received by the optical sensors after being transmitted. Changes in the received light may relate to or be appreciated as an impact of the light contacting a user's anatomy (e.g., muscle tissue). The changes in the emitted light may relate to one or more optical properties of biological tissues. Some examples of optical properties may include absorption, refraction, reflection, and scattering of light. Optical properties may relate to determinable characteristics of the tissue contacted by the emitted light.

In some examples, changes in the emitted light may include refraction of the light passing through the user's anatomy. For example, a change of the emitted light may be a function of a refractive index (RI). RI is a characteristic optical variable that controls the propagation of light in the medium (e.g., biological tissues). A measurement of RI of a biological tissue (e.g., adipose tissue), can be associated with the thickness, composition, density, etc. of the tissue as a factor of the change in velocity of the light passing through it. For example, one or more of the optical sensors of the EMS apparatus, described herein, may emit light with an initial velocity through one or more layers of tissues of the user's body. When the light passes through a layer of tissue, an initial velocity can be observed by the optical sensor and a modified velocity may be observed based on the change in velocity as the light passes through each layer of tissue. Considering adipose tissue, the optical sensors may emit light that can penetrate the user's skin and continue through subcutaneous adipose tissue (SAT) to muscle tissue, where the light has a velocity at a point of initial contact with the SAT and/or muscle tissue. The velocity of the light may change (e.g., decrease) as the light passes through the adipose tissue and the change in velocity can be acquired by the optical sensors. In some examples, changes in the emitted light may be observed or acquired by the optical sensors at different intervals of distance (e.g., the depth of penetration) and/or time.

In some examples, the optical sensors described herein are adapted to acquire scattered light as a result of the emitted light contacting one or more biological tissues (e.g., muscle tissue). Scattered light analysis by the EMS apparatus described herein may relate to the impact of a biological tissue on emitted light causing light particles to scatter upon contact with various tissues structures (e.g., cells, fibers, extracellular matricies, etc.). For example, the light emitted by an optical sensor transmission element may have initial light attributes (e.g., wavelength, frequency, intensity, etc.). As the emitted light contacts or engages biological tissue (e.g., muscle tissue or muscle fibers), particles from the emitted light may be scattered by the tissue and the optical sensors may acquire or sense the scattered light particles. Attributes of the acquired scattered light (e.g., vectors, reflection angles, velocity, quantity, concentration, etc.) may provide data input for quantification of one or more characteristics of the biological tissue (e.g., density of muscle tissue).

In some examples, the optical sensors described herein are adapted to acquire information or data related to the reflection of light emitted into or through biological tissue (e.g., muscle tissue). For example, an optical sensor may emit light that is reflected by one or more layers of biological tissue. The reflected light may be acquired or sensed by the optical sensors and data or information such as the angle of reflection, velocity, duration, and other optical properties may be interpreted by the EMS apparatus described herein. Reflection of the emitted light may provide different modifications of the light based on the biological tissue impacting the reflection. For example, muscle tissue may reflect light differently, or the same, as dermal tissue or interstitial tissue. The EMS system can interpret the sensor data to determine specific tissue characteristics (e.g., muscle density).

In some examples, an EMS suit (e.g., an EMS apparatus) may include more than one optical sensors having a transmission element and each transition element may be configured to emit light having attributes unique to the associated transmission element. The unique light attribute values may be interpreted by one or more receiver elements of the optical sensors and incorporated into the data received by each receiver element to distinguish the location of the associated transmission element from which the light was emitted. For example, a first light may be emitted by an optical sensor transmission element having initial light attributes X and penetrate the user's body. After the light contacts one or more biological tissues (e.g., muscle tissue) and particles of initial light attribute X may become scattered and change to attributes Y that can be sensed by optical sensors. The difference of attributes X and attributes Y can be processed within the EMS apparatus (e.g., by the processing unit) to calculate muscle characteristics. The calculated muscle characteristics may then be incorporated into EMS apparatuses and a stimulation regime may be established whereby stimulation is supplied based on the muscle characteristic data.

In some examples, the optical sensors include a transmission element and a receiver element. The transmission element and receiver element may be incorporated into a single sensor unit. The transmission element may be capable of emitting light into or through one or more tissues of the user's body. The receiver element may be capable of receiving light after the light has contacted or otherwise been modified by the one or more biological tissues (e.g., the user's muscle tissue).

In some examples, the light emitted by the optical sensors is a laser light or other form of light adapted to sufficiently penetrate biological tissues (e.g., muscle tissue) for analysis of sensing by the optical sensors and EMS apparatus (e.g., EMS suit).

The EMS apparatus, as described herein, may include one or more bioelectrical sensors to evaluate bioelectric characteristics of biological tissue (e.g., muscle tissue). For example, impedance of the electrical impulse or energy emitted into the biological tissues of the user may related to biological characteristics of the tissue (e.g., muscle tissue). Some examples of bioelectrical sensors may include a transmission element and a receiver element. A bioelectrical sensor transmission element may emit an electrical pulse into, through, across or throughout body tissue of a user. The emitted electrical pulse may penetrate through one or more biological tissues and be modified the composition, orientation, location, type, arrangement, etc. of the biological tissue. For example, muscle tissue density may provide different modifications based on an increased density or a decreased density.

In some examples, the bioelectrical sensors may include a transmission element and a receiver element. The transmission element may be configured to transmit an electrical impulse into, through, and/or across one or more biological tissues. The receiver element may be configured to receive the transmitted electrical impulse after it has contacted or otherwise been modified by one or more biological tissues (e.g., muscle tissue). In some examples, the electrical impulse from the sensor may be modified from initial attributes at the time the impulse is transmitted or emitted from the sensor. The difference in the received impulse may be incorporated or appreciated by the EMS apparatus to determine or calculate a muscle characteristic that can be used to determine and establish the stimulation regime. For example, where a muscle is more dense, the impedance may be greater. The receiver element may accordingly acquire or sense the change in electrical pulse related to increased muscle density and adjust or establish stimulation parameters based on the sensor data.

In some examples, the sensors are ultrasonic sensors having a transmission element and a receiver element. The ultrasonic sensors may be adapted to emit sound of an initial frequency and wavelength into, across, or through one or more biological tissues. The receiver element may be configured to receive the transmitted ultrasonic waves after they have contacted or otherwise been modified by one or more biological tissues (e.g., muscle tissue). In some examples, the ultrasonic waves from the sensor may be modified from initial attributes at the time the ultrasonic waves are transmitted or emitted from the sensor. The difference in the received ultrasonic waves may be incorporated or appreciated by the EMS apparatus to determine or calculate a muscle characteristic that can be used to determine and establish the stimulation regime. For example, where a muscle is more dense, the ultrasonic waves may be decreased or reduced after contacting or passing through the muscle tissue. The receiver element may accordingly acquire or sense the change in ultrasonic waves related to increased muscle density and adjust or establish stimulation parameters based on the sensor data.

In some examples, the sensors coordinate with each other to combine or compile data acquired thereby. The sensors may communicate sensor data and sensor attributes such as sensor location and sensor parameters to compile and/or combine data to be interpreted by the EMS apparatus in the establishment, determination and/or adjustment of the stimulation regime. For example, sensors on the chest of the EMS suit, may communicate information of the pre-determined location, targetable muscle groups, and biological tissue characteristics. In some examples, the energy (e.g., light, sound, electricity, etc.) may be emitted by a first sensors and received by a second sensor. The second sensor may be the same sensor or different sensors. The second sensor may be the same type of sensor as the first sensor or may be a different type of sensor than the first sensor. For example, a first sensor may emit some type of energy on an anterior side or portion of the user that passes through biological tissues to be received on a posterior side or portion of the user.

An EMS apparatus (e.g., EMS suit) may have a measurement system configured to measure user-specific attributes. In some examples, anthropometric measures such as body mass index (BMI) can determine a ratio of a person's weight relative to their height and can be used against ranges from underweight to obese. For example, BMI can be a metric for determining a severity of obesity. Accordingly, an EMS apparatus can be configured to measure (e.g., acquire) a user's BMI. User-specific BMI data may be recorded, transferred, interpreted, etc. by the EMS apparatus for the determination and/or adjustment of stimulation supplied according to the stimulation protocol. In some examples, user-specific BMI data can be determined away from the EMS suit and the data input into the EMS system, or into a database accessible by the EMS apparatus. For example, BMI may be determined using a series of caliper measurements including a user's height, age, weight, etc. and the data input into a remote device in communication with the EMS apparatus.

In some examples, Percent body fat (PBF) can be a metric for determining severity of obesity. Accordingly, an EMS apparatus can be configured to measure (e.g., acquire) a user's PBF. User-specific PBF data may be recorded, transferred, interpreted, etc. by the EMS apparatus for the determination and/or adjustment of stimulation supplied according to the stimulation protocol. In some examples, user-specific BMI data can be determined away from the EMS suit and the data input into the EMS system, or into a database accessible by the EMS apparatus. For example, PBF may be determined using a series of circumferential measurements including one or more circumferences of a user's neck, abdomen, waist, hips, legs, arms, etc. can be used to calculate PBF. In some examples, the calculation of PBF may also include the user's height, age, weight, etc. and the data input into a remote device in communication with the EMS apparatus. In some examples, the EMS apparatus may have a PBF measurement system configured to acquire circumferential user-specific data as the user engages the EMS apparatus (e.g., the EMS suit).

In some examples, the EMS apparatus described herein may be in operable communication with a dual energy X-ray absorptiometry (DEXA) scanning system for the measurement of body composition including body fat, bone density, muscle attributes, etc. Data acquired by the DEXA scan may be incorporated in the EMS apparatus and interpreted for the development, application, adjustment, etc. of the electrical stimulation supplied to the user.

In some examples, the EMS apparatus described herein may include a processing unit operably coupled to the sensors. The processing unit may be adapted to interpret the data or information acquired or sensed by the sensors. For example, the processing unit may be adapted to incorporated sensor data into one or more algorithms for the quantification of a tissue characteristic (e.g., muscle tissue density). In some examples, the processing unit may be adapted to include one or more coefficients for the interpretation of the sensor data. In some examples, the coefficients are predetermined based on known quantitative analysis of optical properties of the biological tissues (e.g., muscle tissue). In some examples, coefficients, as described herein, may be established based on training the algorithms over a period of time beginning with the user engaging the EMS suit. For example, a user may engage the EMS suit and the sensors may begin to acquire data from one or more sensors. The data may be interpreted into an initial algorithm that is modified over a period of time until sufficient calculations provide for a user-specific coefficient that can be applied to subsequent user engagement.

The stimulation regime or treatment protocol may be developed or established based on the interpretation of sensor data. Stimulation intensity, duration, arrangement, frequency, etc. may be modified based on the sensor data or interpretation of the sensor data by the EMS apparatus (e.g., the processing unit). For example, the optical sensors may obtain data related to the optical characteristics of muscle tissue contacted by light emitted from an optical sensor. The optical characteristic may provide data for determining the muscle density of the user and the muscle density value may provide for a user-specific modification to the stimulation regime. The stimulation regime may provide for increased intensity, higher frequency, shorter pulse duration, for muscle tissue that is more dense. Each factor or aspect of the stimulation regime may be adapted to the user-specific muscle characteristics to provide optimal stimulation of one or more muscles. In some examples, the stimulation regime may be more intense or less intense based on optimized electrical stimulation for the sensed muscle characteristics. Another example may include the bioelectrical sensors obtaining data related to the bioelectrical characteristics of muscle tissue contacted by electrical pulse emitted from a bioelectrical sensor. The bioelectrical characteristic may provide data for determining the muscle density of the user and the muscle density value may provide for a user-specific modification to the stimulation regime.

In some examples, the stimulation parameters of a stimulation regime may be adjusted by sensor data while the user is engaging the EMS apparatus. Sensors may continuously acquire data over a period of time and the data may result in adjustments to the stimulation regime or parameters of the stimulation regime or both. For example, sensed increased in muscle density may increase stimulation parameters to increase the stimulation supplied by the electrodes.

The EMS apparatuses may include an integrated controller and power supply, including an integrated controller and power supply with a user input/output (e.g., touchscreen) that is compact and may be coupled to an EMS suit for controlling the suit and/or for communicating with one or more remote servers. Also described herein are EMS apparatuses having wettable electrical contacts that are adapted for reliable and easy use by the wearer of the suit (e.g., in an at-home or studio setting). Also described herein are EMS suit apparatuses that are easier to put on, adjust and maneuver in than traditional EMS suits, and may allow movement and flexibility while maintaining reliable and sufficient contact between the user and the multiple EMS electrodes. Any of the apparatuses described herein may include a user interface configured to enhance the ease of operation and effectiveness of an EMS suit. For example, described herein are apparatuses (e.g., systems) that may be used to regulate the safe and effective operation of the EMS suit, including limiting or preventing operation in ways that may be less effective and/or dangerous to the user.

In some examples, one or more sensors acquire data to be incorporated into an algorithm for computing one or more user-specific muscle properties. For example, one or more of the sensors may acquire dimensions of a muscle based on the changes in energy (e.g., light, sound, ultrasonic vibrations, etc.) from the transmission element to the receiver element after the energy has been modified based on contact with muscle tissue. Initial values or attributes of the energy signal transmitted into and/or through the tissue of the user may be different that the terminal values or attributes of the energy received by the receiver element. The different in energy attribute values may be input to an algorithm adapted to generate one or more functional values used in development and/or execution of the stimulation regime (e.g., the duration, intensity, sequence, stimulation arrangement, etc.). For example, muscle thickness and/or muscle density may be a muscle characteristic relating to the stimulation regime. A transmission element of a sensor may emit a signal through the user's dermal layers until the first incidence of the signal contacting the muscle tissue. At the first incidence of contact, the signal may be changed distance from sensor to beginning of the muscle tissue and the is the (time elapsed from the sensor sending then receiving a sound/energy pulse X the speed of sound)/2.

In general, an EMS apparatus may include an EMS suit having a plurality of electrodes coupled or couplable thereto, wherein the electrodes are positioned/positionable on the EMS suit in an arrangement that provide muscle stimulation while preventing dangerous (e.g., transthoracic flow) of electrical current through a body of a user wearing the EMS suit during operation of the EMS suit. Individual electrodes of the EMS suit may be controllable by a processor(s) to deliver electrical impulses to muscles of a user who is wearing the EMS suit. In some examples, the processor controls the electrodes based on data and information received from the sensors. When an electrical impulse is delivered via a pair of electrodes, electrical current (i.e., the flow of charged particles) flows from one electrode (of the pair), through a portion of the user's body (e.g., through muscle tissue underlying the pair of electrodes), and to the other electrode (of the pair). The user's body completes an electrical circuit that includes the pair of electrodes, thereby allowing electrical current to flow between the pair of electrodes during operation of the EMS suit, as electrical impulses are delivered via the electrodes. A pair of electrodes may include two electrodes that correspond to a common channel of multiple channels that are used to deliver electrical impulses, channel-by-channel, during operation of the EMS suit. A pair of electrodes may also include two electrodes that allow for electrical current to flow therebetween during operation of the EMS suit, one electrode of the pair operating as a positive electrode (anode) and the other electrode of the pair operating as a negative electrode (cathode). With alternating current (AC), each electrode of a given pair may reverse current with each cycle (or frame). That is, each electrode may change from a positive electrode (anode) to a negative electrode (cathode) with each cycle (or frame).

For example, FIGS. 1A-1F illustrate an example of an EMS system as described herein. This example shows a wireless, whole-body electrical muscle stimulation (EMS) system that includes a suit/vest, a lower body (pants/shorts) portion, a combined power supply/controller/user interface, and an electrode wetting source (e.g., spray bottle). FIG. 1A shows an example of an upper 101 and lower 103 under suit. The under suit may be configured to allow electrical connection between electrodes and the underlying skin in the appropriate region of the body (e.g., over the target muscle groups). For example, the under suit may include openings and/or electrically conductive regions (or may be wholly conductive). The under suit may be configured to conform to the patient's body, e.g., as a stretch and/or compression garment. The under suit may be washable.

FIG. 1B shows an example of an upper torso (e.g., vest) portion 105 of the EMS suit and a lower body 107 portion of the EMS suit. The upper torso portion and the lower body portion may support the plurality of electrodes 109, which may be integrated into the apparatus. These electrodes, as described in greater detail below, may be wettable electrodes adapted to be easily wetted by the user. The upper torso and lower body portions may include one more adjustable straps allowing the user to attach and adjust the fit. The upper torso 105 portion shown in FIG. 1B is configured as a vest, and the lower body region is configured as a chaps-like configuration to be worn over the under suit. In some examples the under suit and the upper torso and lower body regions may be integrated together into a single garment, as shown in FIGS. 4A-4B, below.

In any of these examples the EMS suit may have electrodes strategically positioned so as to apply EMS to the target muscle groups, such as the quadriceps (quads), hamstrings, glutes, abs, chest, lower back, mid back, upper back (trapezius), biceps and triceps, and/or calves.

In any of these examples, the electrical connectors (e.g., "cables") may be integrated into the suit. For example, coupling the power supply/controller into the suit may automatically couple the electrodes to the power source/controller via a single (e.g., multiplexed) connection, dramatically simplifying the contact. For example, the integrated electrical connectors may be coupled via internal cabling that is arranged so as not to limit freedom of movement.

The electrodes of the EMS suit may be arranged in the EMS suit to cover parts of the user's body in order to excite particular muscle groups (e.g., arms, legs, chest, abdominals, back, etc.) through the delivery of electrical impulses that stimulate the muscle tissue beneath the user's skin. In particular, as will be described in greater detail below, the electrodes described herein may be arranged in a manner that increases the ability of the electrodes to remain in reliable communication with the patient's skin and therefore provide energy to the underlying muscle during a treatment.

In some examples, the EMS suit can be configured to increase compliance with treatment (e.g., stimulation protocol) as it may be engaged by the user such that the user wears one or more elements of the EMS suit during use. In some examples, the EMS suit may operate autonomously in a manner to reduce or eliminate a need for manual user input to promote engagement and compliance with the stimulation protocol.

For example, upper body portion (e.g., torso, including chest, vest, etc.) may be worn on an upper trunk of the user's body. The upper body portion may be coupled to the lower body portion, e.g., via one or more mechanical and/or electrical connectors. Thus any of the buckles/straps shown may include both mechanical and electrical connectors.

In any of these apparatuses the connectors 111 (e.g., buckles) may be configured to make and/or confirm electrical connection. For example, the power source/controller may sense and/or confirm that each connector is coupled and/or secured. The controller may, for example, provide a test current/pulse to confirm the electrical connection (via. the electrical properties of the connection, showing an open circuit if not properly attached). The electrical contact with the skin of the user may similarly or additionally be confirmed by the system and may be used as part of a after interlock and/or power-saving protocol.

In some examples the upper body portion may comprise a left front portion, a right front portion, and a back portion. In some embodiments, the left front portion has a first pair of electrodes positioned on an inner surface of the left front portion and within a top half of the left front portion, while the right front portion has a second pair of electrodes positioned on an inner surface of the right front portion and within a top half of the right front portion. In this manner, when the body of a user is wearing the EMS suit, the first pair of electrodes may be disposed on (or atop) one or more left pectoral muscles of the body, and the first pair of electrodes may, therefore, be positioned on a first (e.g., left) side of a midsagittal plane of the body, as well as on a first (e.g., front) side of the frontal plane of the body. A second pair of electrodes may be disposed on (or atop) one or more right pectoral muscles of the body, and the second pair of electrodes may be positioned on a second (e.g., right) side of the midsagittal plane of the body, as well as on the first (e.g., front) side of the frontal plane of the body.

Electrical impulses may be delivered by the respective pairs of electrodes so that the flow of electrical current is primarily passed between each pair of electrodes, though the target muscle region, so that electrical current does not flow between an electrode of the first pair of electrodes and an electrode of the second pair of electrodes, or any other pair, in order to avoid applying electrical energy to regions that are not intended to be stimulated. For example, the apparatuses described herein may prevent electrical current from flow across the midsagittal plane of the user's body in a region of the thoracic cavity during operation of the EMS suit.

FIG. 1C also illustrates an example of an integrated controller/power supply 113. In this example, the integrated power supply/controller includes a separate mechanical and electrical connector; however in some examples the same connector may make both mechanical and electrical connection with the EMS suit. For example, in FIG. 1C the apparatus includes a pair of electrical connectors 115 that may attach to electrical coupling contacts on the suit. In FIGS. 1A-1F only a single pair (e.g., anode/cathode) of connectors are shown. In some examples, multiple connectors/contacts may be used. In this example the suit may include an integrated multiplexing electrical manifold that may direct and/or switch the applied energy to the one or more pairs of electrodes to which power is to be applied to apply EMS. In general, power may be applied to individual pairs of electrodes at a time (sequentially) or in a manner so that nearby electrodes in communication with the body are not concurrently activated by the application of electrical energy. The power supply/controller 113 may be held to the EMS suit by a pocket and/or a mechanical connector such as Velcro, straps, etc. Multiple mechanical connectors may be included.

FIGS. 1D and 1E illustrate examples of arm electrode supports 119 including electrodes 109 that may be used to apply electrical energy to the biceps and/or triceps. In this example, in which the arm electrode supports are not integral with the upper/torso portion 105, addition external cables 121 may be used to connect the arm electrodes to contact 117 on the upper/torso portion (vest) 105. Alternatively in some examples the electrode and/or electrode supports may be integrated into an upper/torso EMS garment.

In any of these apparatuses, the back of the upper body portion of the EMS suit may include multiple electrodes 109, including, e.g., a third pair of electrodes positioned on an inner surface of the back portion and within a left half of the back portion, and a fourth pair of electrodes positioned on the inner surface of the back portion and within a right half of the back portion. When the body of a user is wearing the EMS suit, the third pair of electrodes may be disposed on (or atop) one or more left back muscles of the body, and the third pair of electrodes may, therefore, be positioned on the first (e.g., left) side of a midsagittal plane of the body, as well as on a second (e.g., back) side of the frontal plane of the body. Meanwhile, the fourth pair of electrodes may be disposed on (or atop) one or more right back muscles of the body, and the fourth pair of electrodes may, therefore, be positioned on the second (e.g., right) side of the midsagittal plane of the body, as well as on the second (e.g., back) side of the frontal plane of the body. Other configurations and arrangements may be used.

Any of the electrodes described herein may be wettable electrodes that include an absorbent substrate (forming a fluid/wetting reservoir) in electrical communication with the electrode and configured to contact the user's skin (either directly or through the under suit). These wettable electrodes are configured to hold a conductive fluid (e.g., water, including saline) that may help make a reliable electrical contact with the user's skin, and maintain the electrical properties, even as the user sweats during physical exercise wearing the EMS suit. This may be particularly helpful, as these wettable electrodes may be configured (by size and position) to allow continuous electrical contact with the skin without having the electrical properties significantly change doe to sweating. The electrode assembly may also include one or more ports or opening configured to mate with the fluid source 125 (e.g., such as the spray bottle shown as an example in FIG. 1F). to allow delivery of the conductive fluid (e.g., saline) to the fluid reservoir. For example, each electrode assembly may include a port on an outward-facing side to which the fluid source may be engaged to apply (e.g., by spraying) fluid. The fluid port may also be configured to prevent leakage of fluid (e.g., saline) out of the port and/or out of the electrode assembly. The electrode assembly may include the fluid reservoir, which may be a porous material (e.g., sponge and/or wettable hydrogel, etc.).

The apparatus shown in FIGS. 1A-1F does not show the associated application or other components of the apparatus that may be used to control the applied power to drive EMS of target muscle(s). The controller 113 may include a user interface (e.g., touchscreen) for direct communication with the user and/or it may be configured to wirelessly communicate with one or more external processors, such as a smartphone, tablet, computer, etc. In some examples the user may communicate via a smartphone or tablet (not shown). In some examples the user may communicate with a remote processor. Any of all of the controller/power supply, smartphone, and/or remote processor may include software, firmware and/or hardware for engaging with the user and/or for controlling operation of the apparatus, including for engaging in one or more safety protocols to prevent a user from exceeding a predetermined or calculated amount of EMS to individual body regions (muscled) and/or the entire body based on the user's condition and prior operation of one or more EMS apparatuses.

Figure 2A:
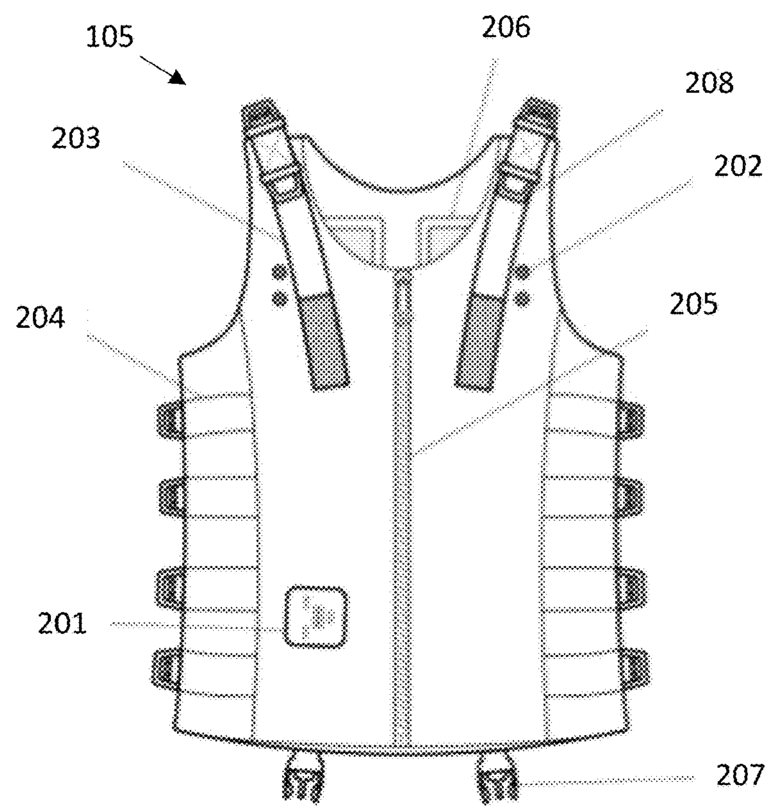

FIG. 2A shows an example of an upper torso portion 105. In this example, the upper torso portion includes a connector port 201 that may coupe with an integrated controller/power supply (not shown). The apparatus also includes a plurality of mechanical connectors (e.g., clasps, snaps, etc.) 202, and a plurality of adjustable straps (e.g., Velcro straps) 203, including side straps 204. The upper torso portion in this example also includes a zipper 205. A plurality of electrode pads 206 may also be integrated into the upper torso portion. The apparatus may also include connectors (e.g., buckles) 207 for coupling to a lower portion. Any of these connectors and/or straps may be adjustable and may include retainers 208.

Figure 2B:
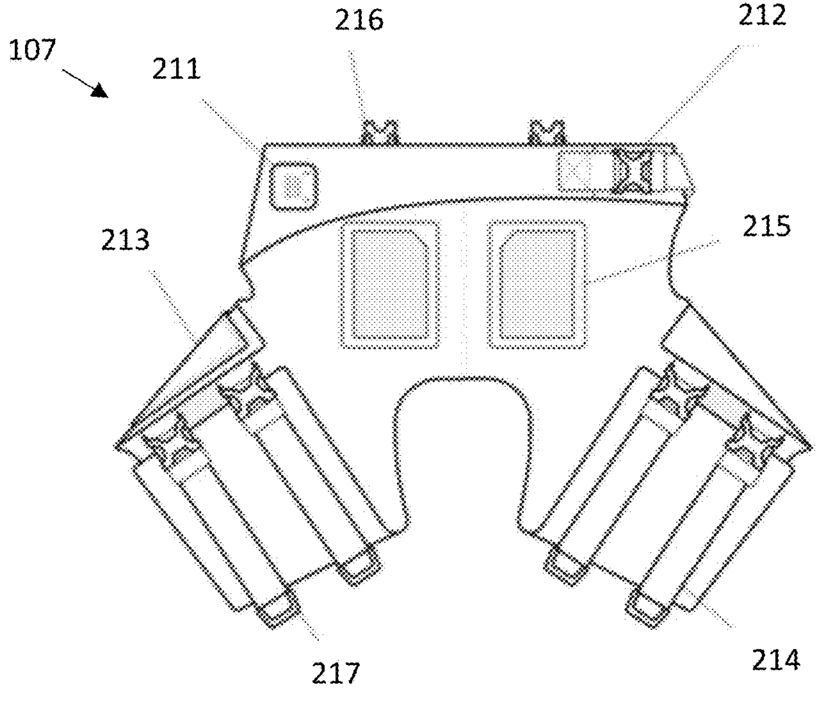

FIG. 2B shows an example of a lower portion 107. The lower portion may also include one or more mechanical and/or electrical connectors 216 for coupling to an upper portion (onto which a power supply/controller may be attached). Alternatively or additionally the lower portion may hold the controller/power supply (and may provide power and control operation of the upper portion(s)). For example, the lower portion may include a pocket and/or attachment site 213 for the controller/power supply and/or may include a connector port 211. The lower portion may include a hip belt 212 for securing the apparatus to waist (e.g., onto or over an under suit). In some examples the apparatus may include adjustable straps and/or buckles and/or other components to adjust the fit 216. The lower portion may also include one or more electrode assemblies (including electrical pads 215) for applying EMS to a muscle/muscle group on the lower body.

FIG. 2C illustrates an example of an arm electrode support 119 shown from the top 229 and bottom 228 (user-contacting side). The arm electrode support may include one or more attachments (e.g., straps 221) including loops 223 and/or Velcro attachment portions 224. The arm electrode support may also include one or more electrode assemblies 222.

FIGS. 3A and 3B illustrate examples of EMS suits as described herein, worn on a user. In FIG. 3A the EMS suit including all of the components described above, including an upper portion 305, a lower portion 307. The upper and lower portions are coupled together, and a power supply/controller 350 is shown coupled to the lower portion. The user is also wearing an upper 301 and lower 303 under suit.

The EMS suits shown may include electrodes on the legs, e.g., quadriceps, buttocks, lumbar region, back, trapezious, and one or more on the abdomen, pectorals, and arms. The positions may be adjustable, within a predetermined or arbitrary range. For example, on the legs, the lower portion may be configured to allow adjustment of the position(s) of the electrodes in one or two positions, such as over the medial thigh muscle or the medial and lateral muscles. Electrodes may be positioned between 5 cm and 10 cm apart. In another example, the apparatus may be configured to allow adjustment of the position of the muscles of the abdomen, including adjusting the pairs of electrodes to be further or closer apart. The central abdomen may be adjusted and/or a more laterally separated position may be used.

FIGS. 4A-4B illustrate another example of an EMS suit apparatus similar to that described above, in which an under suit may not be needed. In this example, the apparatuses include a wetsuit-like appearance, and may be formed, at least in part of an elastic material, such as a polymeric material (e.g., neoprene, etc.) that is breathable, and is configured to hold the electrodes (e.g., the electrode assemblies) in contact with the skin. For example, in FIGS. 4A and 4B, the EMS suit may include an upper 405 and a lower 407 portion, or may be a unitary suite (e.g., integrated upper and lower portion). The suite may be formed of an elastic fabric and includes a closing system 447 (e.g., zipper). The electrode assemblies may be integrated into the suit but may be configured to allow selection of one or more alternative positions, e.g., to allow the user to adjust the separation the anode and cathode electrodes. Thus, the electrodes may include an input (e.g., strap, selector, etc.) for allowing or locking internal movement of the electrode assembly position. As mentioned above, any of these electrode assemblies may be configured to allow fluid (e.g., saline) to be applied as part of the electrode assembly. In the example apparatus shown in FIGS. 4A and 4B the electrode may be coupled to the power supply/controller 450 by internal wires (not visible).

In some examples, the electrode assemblies or electrodes described herein may comprise one or more sensors as described herein. For example, FIG. 4B illustrates an exaggerated arrangement of sensors positioned throughout the EMS apparatus. Sensors 412 are shown and examples of sensor elements (e.g., a transmission element or a receiver element) 413 may be positioned at a location on the EMS apparatus to operably communicate with the biological tissues of the user. In some examples, the sensors 412 are integrated or otherwise associated with the electrodes or electrode assemblies. In some examples, the sensors 412 are located or locatable on an interior of the EMS suit such that they contact or are substantially proximal to the user's skin.

As mentioned above, any of these apparatuses may include electrode assemblies configured as wet or wettable electrodes. For example, these apparatuses may be configured so that fluid (e.g., water, saline, etc.) may be added to wet a skin-contacting surface of the electrode assembly. Electrical contact is essential to proper function and control of an EMS apparatus. The electrode assemblies may be wet prior to applying the apparatus and/or after applying the apparatus, and in particular the electrode assemblies including the fluid reservoir regions, e.g., a porous material (e.g., sponge and/or wettable hydrogel, etc.). FIG. 5 illustrates an example of the application of fluid (e.g., water) 567 via a spray bottle to wet electrodes 565 (and in particular, to wet the porous skin-contacting surface of the electrode) on the inside of the suit 563. In some examples the suit may include one or more ports into which a fluid (e.g., water, saline, etc.) may be added. The fluid may be a conductive fluid.

Any of the apparatuses described herein may include one or more temperature elements configured to regulate a temperature deliverable to the user. For example, one or more electrodes may be a heating element configured to supply heat as a parameter of the stimulation protocol. Heat supplied by the EMS apparatus to the user may increase a thermogenic processes.

Any of the apparatuses described herein may include sensors, e.g., motion sensors, position sensors, etc. that may confirm the position and/or activity of the user. Sensors may be included with the one or more electrodes and/or may be included with the controller (or power supply and/or controller, including integrated power supply/controller). The sensor(s) such as an accelerometer, may be used to confirm that the user is performing a predetermined action/exercise (as described below) and may therefore coordinate the application of the EMS with the prescribed movement(s). The sensor(s) may also be used as a safety trigger, for example, stopping or pausing (or in some cases decreasing) the application of EMS based on the sensed motion and/or position.

In general, the suits described herein may be cleaned and maintained by the user. For example, the suits may be treated with an antibacterial solution and rinsed with water. An anti-odor product may be applied following each use, and/or after applying the antibacterial solution. The suit may be dried, e.g., by handling in a drying area. An air-drying system may be used to expedite drying. Heated or room-temperature air may be used to dry the suit. In general, the suit may be washed, e.g., by soaking in a soapy solution at low concentrations. The suit may be washed and/or rinsed in cold water to clean (including removing excess salts from the added fluid and/or sweat).

Figure 6:
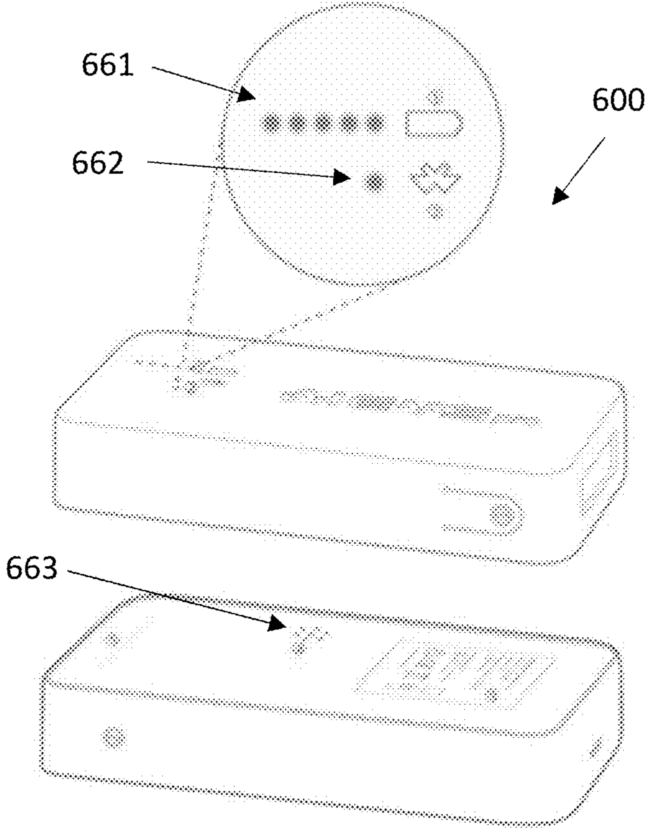
FIG. 6 shows one example of a power supply for an EMS apparatus.

Also described herein are power sources and/or combined power sources (e.g., batteries) and controllers. FIG. 6 illustrates one example of a power source (e.g., battery) 600. This example may be used with an apparatus as shown herein and may include a simple user interface showing power level 661, wireless connectivity 662 (e.g., Bluetooth connection), etc. In some examples, described in greater detail below, additional user interface information (e.g., touchscreen) may be included. Any of these apparatuses may include an audio output 663 (e.g., speaker) that may be used as an output. The power source/controller may be, e.g., 500 g or less (e.g., 450 g or less, 400 g or less, 350 g or less, 300 g or less, 250 g or less, etc.). The apparatus may be relatively small (e.g., 20×10×5 cm or less, 18×8×3 cm or less, 16.5×8×3 cm or less, etc.). The apparatus may also include an on/off button that may be manually or automatically controlled. Any of these power sources may be configured as batteries, such as lithium ion (Li-Ion) batteries. The power source may include a charging port (e.g., mini-USB port). In some examples the power source may also or additionally include a port for connecting to the EMS suit, and/or a cable connected to the EMS suit. As mentioned above, in some examples the power source (or power source/controller) may be configured to be secured within a pocket in the suite and may electrically couple to the suit while within the pocket.

Any of these power sources and power source/controllers may include one or more emergency shutoff controls, or an override shutoff control. The shutoff control may be configured to immediately stop the application of power to the electrodes. In some configuration the shutoff control may be configured to completely shut off the apparatus; in other examples, the shutoff control may continue sensing/monitoring and processor functions but may disable the application of power to any of the electrodes (e.g., for delivery of EMS) until a rest condition is satisfied. For example, in some examples an emergency shutoff control (or an override shutoff control) may be included on the outer surface of the battery or battery/controller. In some examples the suit may have an integrated shutoff control on the front outer surface of the suit that may be easily actuated by the user.

Any of these suits may include one or more sensors (e.g., physiological sensors), including heart rate sensors, pulse oxygenation sensors, respiratory sensors, etc. In some examples the apparatus may be configured to trigger a safety shutoff of EMS if the sensors detect user physiological signals that exceed a predetermined safety threshold. For example, if the heart rate exceeds, e.g., 180 bpm (e.g., 155 bpm, 160 bpm, 165 bp, 170 bpm, 175 bpm, 180 bpm, 190 bpm, 195 bpm, 200 bpm, 205 bpm, etc.), and/or if the blood pressure exceeds a predetermine range, etc.

FIGS. 7A-7D illustrate one example of a combined power source/controller 700. In this example the combined power source/controller including a touchscreen input 771, and may include one or more additional inputs 772, including an emergency shutoff control. The combined power source/controller may also include an attachment (input) 775 for coupling to a charging source and/or for coupling to an input/output (including a cable input/output) on the EMS suit. FIGS. 8A-8E show another example of a combined power source/controller 800 similar to that shown in FIGS. 7A-7D, also including a display screen (which may optionally be a touchscreen) 871 and one or more inputs 872, including, e.g., an emergency shutoff control. FIGS. 9A-9F shown another example of a combined power source/controller including a display 971 and inputs 972. This example also shows nan interface or adapter 976 for coupling to the EMS suit and/or a charger for charging the power supply integrated with the controller.

FIG. 10 shows an image of a prototype combined power source/controller 1000, with the outer housing removed, showing the display screen 1071 and inputs 1072 visible. The controller may include one or more processors, memory, timer(s), and control circuitry, including wireless circuitry and/or power control circuitry.

Figure 11:
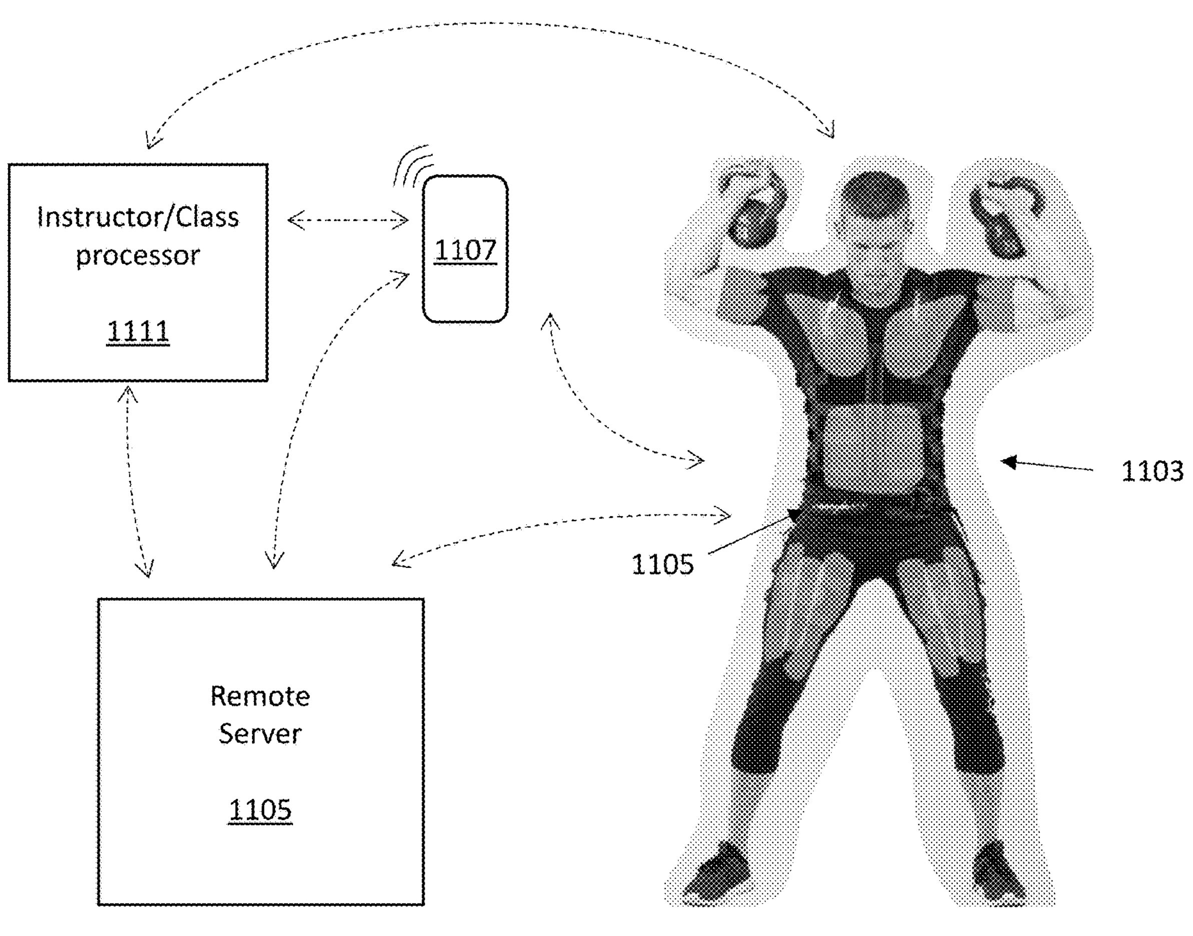
FIG. 11 schematically illustrates one example of an EMS apparatus as described herein.

FIG. 11 illustrates one example of an EMS apparatus, including an EMS suit 1103, including a controller/power source that may operate with software on one or more of a user device (e.g., smartphone 1107), remote server 1105 and/or an instructor (or class) processor 1111. In FIG. 11, the EMS suit 1103 may be controlled by a worn controller 1105. The locally worn (EMS suit) controller may include the safety override control and may generally control the application of EMS to the electrodes/electrode assemblies in the suit, as described above. The locally worn controller (e.g., an integrated power supply/controller 1105) may communicate wirelessly, e.g., via Bluetooth (or other wireless technique) to any of the user device 1107, instructor/class processor 1111 and/or remote server. For example, the suit, which may be identified by a unique identifier associated with the user (e.g., name, number, address, etc.) may receive instructions for delivering a predetermined EMS protocol corresponding to a desired training regimen. The protocol may be delivered by the local controller but may be run in combination with the remote server, instructor class/server (for example, for group exercise) or from the user device (e.g., smartphone 1111).

In particular, the apparatus may be configured so that during a training episode, a selected or prescribed training regimen may be provided to the user, instructing the user to perform one or more actions. As mentioned above, a sensor, e.g., a motion sensor (e.g., accelerometer) may be included as part of a combined power source/controller and the controller may confirm that the user has begun, is in the midst of continuing to perform, or has completed, a prescribed movement before applying or continuing the application of EMS.

In general, the application of EMS may be targeted to a particular set of muscles or muscle groups corresponding to a particular activity. For example, the apparatus may be configured to apply a workout targeting a particular user goal, such as increasing endurance, mobility, and/or strength. These workouts may include a defined set of movement or actions (e.g., exercises, yoga/stretching poses or movements, etc.) and may be presented to the user concurrently with the application of EMS to one or more muscles (or muscle groups) related to the movements or actions.

For example, strength training routines may include resistance exercises (weights, bands, bodyweight, etc.), core strength, high-intensity interval training, etc., and may target specific muscles. The apparatus may automatically apply EMS in a coordinated manner with the presentation (and presumed performance) of the movements and/or may detect the user's movements and apply EMS when the user is performing the appropriate corresponding movement or shortly thereafter. In some examples the apparatus may therefore provide immediate feedback to the user that the movement is being performed within a desired level of activity, further reinforcing the effects of the EMS.

In any of these apparatuses, the intensity of the apparatus may be automatically adjusted to either adjust the applied EMS or to set the range of EMS intensities within which the user may select intensities (e.g., high, medium, low, off, or X % of 100%, where the range of 100% is set automatically by the system).

In particular, the apparatuses described herein may control and/or set the maximum EMS power/intensity that may be applied to a particular user based at least in part on one or more of: (1) an initial baseline (e.g., starting baseline) for the user; (2) the user-provided input(s); and (3) the historical (including within the last z hours or days) application of EMS by the same user. The apparatus may control the applied EMS power/intensity specific to each muscle or muscle group (e.g., the maximum intensity/power applied to the quadriceps may be different from the maximum power/intensity applied to the biceps, for example). Alternatively, the maximum power/intensity of the EMS applied may be the same across all muscles/muscle groups. The apparatuses described herein may adjust the EMS power/intensity by adjusting one or more of the pulse frequency applied (e.g., between 0/off and 120 Hz, e.g., between 0-100 Hz, between 50-120 Hz, between 60-120 Hz, between 70-120 Hz, between 80-100 Hz, between 70-100 Hz, etc.), the current applied (e.g., between about 0.2-120 milliamps (mA), between about 1-90 mA, between about 1-100 mA, between about 5-110 mA, between about 1-120 mA, etc. or any range within these), the pulse width (e.g., between about 100 microseconds (s) to about 500 s, between about 200 s to about 450 s, between about 150 s to about 400 s, or any ranges therebetween). In some examples the EMS power/intensity may be modulated by adjusting the ramp-up time (time to ramp up to a maximum applied current) and/or by adjusting the frequency within an application session (increasing or decreasing the frequency).

In some examples, the automatic adjustment of the intensity or the stimulation parameters or stimulation regime may be adjusted based on information acquired by the sensors (e.g., optical ultrasonic, electrical sensors). In some examples, the adjustment may be triggered based on a predetermined interval or duration of stimulation. In other examples, the user may be able to selectively engage the controller to initiate an update or adjustment procedure including the operation of the sensors to acquire data and provide updated sensor data for processing by the EMS apparatus that can be used for adjustment.

In general, the apparatuses described herein may be configured to apply power to just a subset of the electrodes (e.g., muscles or muscle groups) and may apply power to separate sets of electrodes corresponding to different muscles in an alternating manner, to avoid concurrent stimulation of multiple sets of electrodes.

The apparatuses described herein may be configured to safely apply EMS by controlling the applied energy (e.g., frequency and/or current and/or pulse width and/or ramp-up/ramp down time) based on a combination of on one or more of: (1) an initial baseline (e.g., starting baseline) for the user; (2) the user-provided input(s); and (3) the historical (including within the last z hours or days) application of EMS by the same user. In particular the apparatuses described herein may automatically set the maximum applied EMS power and/or intensity by estimating a maximum specific to a particular user base on the user's specific baseline and the user's recent (e.g., within the last z hours, where z is between about 8 hours or less, about 24 hours or less, about 36 hours or less, about 48 hours or less, about 60 hours or less, about 72 hours or less, etc.).

An initial baseline may be set based on a user's initial response to questions, such as the user's age, fitness level, general or specific health concerns, etc. In some examples the apparatus may perform an automated question and answer/testing session to set a baseline/initial user level. For example, the user may respond to questions regarding their ability to feel certain EMS inputs one or more (or all) of the electrodes. The user may also be asked to perform various actions (e.g., exercises) while wearing the apparatus and/or without wearing the apparatus and may provide feedback by self-reporting or via one or more sensors (e.g., heart rate, pulse oxygenation, accelerometer/position sensors, etc.).

The baseline data may be estimated, and an initial maximum level of EMS intensity/power may be determined. The initial baseline may be determined from population data of similarly-situated users (e.g., by age group, gender, health, weight, height, etc.). Initial baseline data may be set in part based on user-reported response to a variety of different EMS stimulation levels for each (or a subset of) muscles/muscle groups.

A dataset for each user may be maintained locally (e.g., on the user-specific EMS suit/controller) and/or may be kept in a remote database and accessed by the user-specific EMS. The user information (data) may include specific responses to the initial baseline data collection and/or the initial baseline values estimated by the system, including initial baseline values specific to each muscle or a subset of muscles). In some cases, initial baseline values for different muscles may be determined based on a patient-specific estimate for one or more muscles (e.g., quadriceps, biceps, pectorals, etc.).

User-specific baseline data may be adjusted periodically. User-specific data may be secured. For example, if user-specific date is recorded in a remote database it may be anonymous and indexed by a separately secured key corresponding to a particular user. In some cases, baseline information may be specific to an EMS system (e.g., EMS suit) and/or specific to a user. A user may be uniquely associated with a particular EMS suit).

The maximum EMS intensity/power that may be applied to the user may be adjusted with operation of the system. In general, the initial (e.g., baseline) EMS intensity/power may be set low, to avoid harming the user. With consistent use, the maximum intensity may be adjusted. For example, the apparatus may be configured to increase the maximum intensity with regular use and/or with user-requested increase.

As a safety, any of the apparatuses described herein may reduce and/or reset the maximum if EMS is not applied within a particular timeframe (e.g., if it has been more than x hours or days since the last EMS use). For example, for every x hours that the user has not operated the EMS apparatus the maximum intensity/power may be scaled towards the initial baseline (e.g., if no EMS has been performed by the user within 4 days, 5 days, 6 days, 7 days, 8 days, 9 days, 10 days, 11 days, 12 days, 13 days, 14 days, etc.).

Further, the system may lock out or prevent EMS from being applied more frequently than a predetermined time period. For example, the apparatus may be configured to prevent the user from applying EMS more than one session (or more than a maximum number of minutes or a maximum aggregate energy) every x hours or day (e.g., no more than once per 20 hours, per 24 hours, per 30 hours, per 36 hours, per 40 hours, per 44 hours, per 48 hours, per 52 hours, per 56 hours, per 60 hours, etc.).

Any of the apparatuses described herein may gradually increase the intensity of the EMS (e.g., the power of the EMS), e.g., by increasing one or more of the frequency, pulse width, amplitude, etc., over the course of a treatment session, up to a limit of the maximum intensity. For example, the apparatus may automatically increase the applied EMS power from an initial starting level up to 100% of the maximum EMS power/intensity available to the patient as calculated for a particular session (based on the baseline, historical, and/or user-selected input). In one example, a new user may have a maximum baseline power for their first session of 60 Hz, and a pulse width of about 200 s and an amplitude (which may depend on the electrode parameters) of, e.g., 100 mA. The applied intensity/power may be a function of one or more of these parameters. The apparatus may increase the applied EMS power/intensity from 50% of this value up to the maximum 100% (e.g., starting at 30 Hz and increasing to 60 Hz, etc.), which may be specific to a particular muscle or set of muscles.

Figure 12:
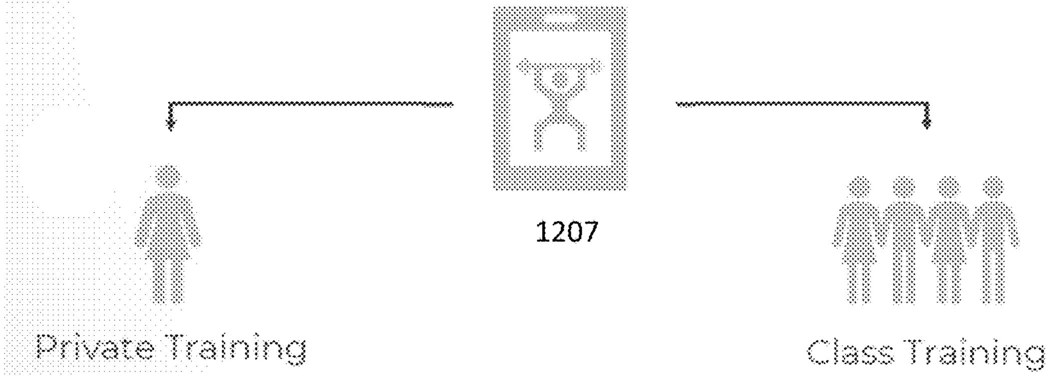
FIG. 12 schematically illustrates an example of a control system (e.g., application software) for an EMS apparatus.

In general, these apparatuses may include software that may perform any of these methods. For example, the software may be an application software (app) that is configured to run on the user's device (e.g., smartphone) and/or on the power supply/controller. The software may be configured to control the EMS to a particular use or to coordinate the control of a group of users that may be exercising together, e.g., as part of a class. For example, FIG. 12 schematically illustrates a user software 1207 that may be used to assist the user in private training or in training a part of a class.

The application software 1207 may allow a user to select a particular training session and/or class and may coordinate the application of the training session and the application of the EMS. In some examples the application software may record the progress and may adjust the maximum possible EMS intensity/power for each session, as described above. The application software may therefore automatically adjust the settings (EMS settings) for each workout.

The sessions ("workouts") may start the EMS with settings based on the individual base settings (baseline) as mentioned above, and the apparatus may optimize the maximum possible EMS intensity and/or power for each setting, as well as the onset of this maximum during the course of a session. As described above, this may therefore be customized to each user and specific to their body and fitness level and configured to prevent harm or discomfort to the user. The apparatus may recalibrate the base settings.

Any of these apparatuses may include a user interface that may be displayed, for example, on the power supply/controller and/or on the user apparatus (e.g., smartphone, television/display, etc.). This user interface may include input/outputs for each of the EMS electrodes and/or corresponding muscle groups, including showing an intensity level (e.g., as frequency, amplitude, pulse width, and/or some combination or derived value of these, e.g., generically "intensity"). The user may be permitted to select a value for each or some of these which may be limited to the maximum level selected or set by the system. The user interface may also show the corresponding positions/movements/exercise and/or may display an instructor or model performing or guiding the user in performing them. In general, the apparatus (e.g., software, firmware, etc.) may coordinate the application of EMS via the EMS suit to the session being performed, including coordinating activating of the appropriate electrodes.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

Applications

In general, any of the EMS apparatuses as described herein may be operated by a user first by the user engaging the EMS apparatus (e.g., EMS suit) and wearing one or more of the EMS suit elements. The one or more electrodes are positioned against the user or in operable communication with one or more anatomic regions of the user during use (e.g., engagement). The EMS apparatus is initiated and electrical stimulation is supply by one or more of the electrodes. In some examples, a controller controls the stimulation supplied by the one or more electrodes by regulating or modulating one or more stimulation parameters. The one or more sensors may begin to acquire data prior to the user engaging the suite. For example, the EMS apparatus may receive user-specific data prior to the user engaging the EMS apparatus. In some examples, the initial user-specific data may be input to the EMS apparatus prior to the user engagement.

The one or more sensors may acquire data (e.g., user-specific data) after the user engages the EMS suit. The user-specific data may be interpreted by the EMS apparatus and a stimulation protocol can be developed. The stimulation protocol may be developed based on the user-specific data and/or may be developed independent from the user-specific data. In some examples, the one or more sensors may acquire data once, continuously, periodically, etc. before, during and/or after use.

In some examples, the stimulation protocol may be amended by the EMS apparatus based on acquired user-specific data. The stimulation protocol may include adjustments to one or more of the stimulation parameters including initiation of stimulation, termination of stimulation, or modification of stimulation supplied by the one or more electrodes.

In some examples, any EMS apparatus described herein may acquire data and transmit the data to and from one or more remote devices.

In some examples, an alert system operably coupled to the EMS apparatus may provide an indication, measure, or other relevant information to the user regarding the stimulation protocol.

In some examples, any method described herein may include the user performing a physical exercise. For example, the user may preform a physical exercise prior to engaging the EMS apparatus, while engaging the EMS apparatus, and/or after performing the EMS apparatus. In some examples, the stimulation protocol may accommodate the physical exercise such that the electrical stimulation may be supplied during a period of physical exercise, during a period between physical exercise (e.g., resting period), or after a period of physical exercise, or a combination thereof.

In some examples, the EMS apparatus as described herein is used as a therapeutic device to increase weight loss (e.g., rate of weight loss and/or quantity of weight loss). Weight loss may be determinable based on changes in apomorphic measurements, BMI, PBF, etc.. Any EMS apparatus described herein may be used as part of a therapeutic application for user's having, suspected of having, at risk of having, or not having a disease or condition related to deficiencies in weight loss, hormone dysregulation, metabolic processes, etc. Therapeutic applications may relate to any disease or condition including diseases or conditions that may be detectable with minimally invasive or non-invasive sensors associated with the EMS apparatus. In some examples, disease profiles may be stored, developed, established, acquired, or otherwise known to the EMS apparatus and can be used to compare or cross-reference the user-specific biometric data obtained by the EMS apparatus via the one or more sensors.

A disease profile may include known characteristics of a disease or condition such as symptoms, risk factors, genetic factors, biological factors, physiological factors, and/or any other relevant information associated with a disease state. The disease profile may provide a similarity score based on the comparison of the disease profile to the user-specific biometric data acquired by the EMS apparatus. For example, a similarity score may indicate a similarity between the observed or acquired user-specific biometric data and the known characteristics of a disease or condition (e.g., hormone dysregulation).

Detection may include identifying a sign or symptom of a condition or disease. The detection may be sufficient to identify factors supporting a prediction of an impending disease-related biological activity. For example, one or more sensors may be configured to acquire perspiration data of a user and the EMS apparatus may interpret the data with data from one or more other sensors to determine, suggest, present, or indicate an underlying condition related to hormone dysregulation. Another example may include more than one sensors acquiring different biometric data that may be combined and interpreted by the processing unit to establish a prediction of impending disease-related biological activity.

For any of the applications of the EMS apparatus described herein, a threshold may be established related to the user-specific biometric data detected by the sensors. A threshold may be a user-specific threshold based on a user engaging the EMS apparatus (e.g., the user wearing the apparatus) for a period of time. In establishing a threshold, the duration of time may begin with a first use as the sensors begin to acquire user-specific data. As data is accumulated by the EMS apparatus, patterns, rhythms, or other natural fluctuations in the user-specific biometric data may be incorporated into establishing a threshold specific to the user. For example, developing a threshold with the EMS apparatus may be a calibration of the EMS apparatus for a specific user.

In some examples, developing a threshold or standard values associated with the biometric data detected by the sensors may be predetermined. For example, known values include a range of values with a minimum and maximum that can be considered to be a healthy state. A healthy state value range may include an upper limit or lower limit associated with the particular biometric factor being evaluated. In some examples, predetermined thresholds may be adjusted or established by an individual (e.g., a healthcare provider) based on known acceptable or healthy-state values for a particular biometric factor.

In some examples, an EMS apparatus as described herein may diagnose a disease or condition. Some illustrative examples of diseases and conditions that may be detectable and/or interpreted by an EMS apparatus described herein for the development and execution of a stimulation protocol may include hypoproteinemia, chronic stress, Cushing's Syndrome, hypothyroidism, polycystic ovary syndrome, syndrome X, menopause, medication side effects, hormone dysregulation, diabetes, cardiovascular disease, metabolic disorders, etc. Diagnosis of a disease or condition may include the EMS suit sensing or analyzing user-specific factors relating to a disease of condition. One or more sensors within the suit may be adapted to receive biological and/or physiological data relating to the user and associated with a sign, symptom or other manifestation of a disease or condition. In some examples, diagnosing a disease or condition may include an EMS stimulation as a test or challenge of one or more biological tissues. The diagnostic EMS challenge may be supplied by one or more electrode assemblies, as described herein. In some examples, the diagnostic EMS challenge may be supplied according to a testing regime based on the user-specific information, predetermined user information, one or more disease profiles, one of more evaluation procedures based on a disease profile, etc. For example, diagnosing a disease with an EMS apparatus as described herein may include a user engaging (e.g., wearing the EMS suit) the EMS apparatus and initiating diagnostic protocols. The one or more sensors may acquire or detect user-specific information and one or more electrode assemblies may supply an electrical pulse or stimulation to challenge or test associated biological tissue (e.g., muscle tissue) which can illicit a physiological response. The response may be detected by one or more sensors and the data may be sent to the processor for interpretation. The processor may interpret the data and compare detected user-specific information against disease profiles to present a diagnosis.

Diagnosis may include input from remote sources (e.g., a healthcare provider). Data acquired by the EMS apparatus may be transmitted for further evaluation to a remote device or database for further consideration. For examples, the user's medications, clinical history, family history, and/or other relevant input from a healthcare provider may be communicated to the EMS apparatus for interpretation and developing the stimulation protocols.

In some examples, an EMS apparatus as described herein may treat a disease or condition. Treatment of a disease or condition may include the EMS suit sensing or analyzing user-specific factors relating to a disease of condition. One or more sensors within the suit may be adapted to receive biological and/or physiological data relating to the user and associated with a sign, symptom or other manifestation of a disease or condition.

Treating a disease with an EMS apparatus, as described herein, may include EMS supplied by one of more electrodes (e.g., electrode assemblies) based on user-specific biometric data. In some examples, the supplied EMS may be dynamically adjusted based on the user-specific biometric data. In some examples, the EMS may be dynamically adjusted based on a known or suspected disease of the user. In some examples, the EMS may be adjustable by the user or by another individual (e.g., a healthcare provider) through engaging the interface of the system to adjust EMS maximum, minimum, or values therebetween.

In some examples, an EMS apparatus as described herein may prevent a disease or condition. In some examples, the stimulation protocols can be configured to increase a rate of weight loss. The decreased period of time to a target weight loss, or decrease in weight (e.g., fat) may prevent diseases and conditions such as cardiovascular disease. In some examples, prevention of a disease or condition may include the EMS suit sensing or analyzing user-specific factors relating to a disease of condition. One or more sensors within the suit may be adapted to receive biological and/or physiological data relating to the user and associated with a sign, symptom or other manifestation of a disease or condition. In some examples, prevention may relate to the prevention of a sign or symptom of a disease or condition. Preventing a disease of condition may include interpretation of user-specific biometric data that is associated with a prediction or evaluation related to impending disease-associated biological activity. For example, the EMS apparatus may acquire user-specific biometric data related to an impending stroke or tremor. After acquiring the data, the EMS apparatus may establish and execute a stimulation regime based on the predicted or observed disease-associated biological activity. By suppling the electrical stimulation prior to or following the disease-associated biological activity, the EMS apparatus may prevent the incidence of the disease-associated biological activity (e.g., the stimulation may prevent or reduce the severity of the stroke).

In general, applying EMS during one or more treatment sessions may increase a rate of weight loss. In some examples, the use of the EMS apparatus and associated electrical stimulation may increase an amount of weight lost. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

Any of the methods and apparatuses described herein may be used for one or more therapeutic indication, such as for physiotherapy by a patient (user) recovering from an injury, surgery, etc. For example, any of the methods and apparatuses described herein may be use to prevent weight gain (e.g., increase in BMI and/or PBF) due to, or after a medical procedure.

In some examples, a user may be obese. For example, the user's BMI may be determined. In some examples, a user's may be obese when their BMI percentile is equal to or greater than 5, 10, 15, 20, 25, 30, 35 or more, including any value therebetween. In some examples, a user may be overweight. For example, the user's BMI may be equal to or greater than 5, 10, 15, 20, 25, 30 or more, including any value therebetween. In some examples, the user's BMI can be equal to or greater than 1, 2, 3, 4, 5, 10, 15, 20, 25, 30, 35, 40 or more, including any value therebetween.

In some examples, a user may be initially classified based on their associated BMI. For example, a user may be considered in Class 1 if their BMI is equal to or greater than 30 to <35. For example, a user may be considered in Class 2 if their BMI is equal to or greater than 35 to <40. For example, a user may be considered in Class 3 if their BMI is equal to or greater than 40 or higher. Class 3 obesity is sometimes categorized as "severe" obesity.

In some examples, any EMS method or apparatus described herein may increase a rate of weight loss compared to physical exercise or no physical exercise alone. In some examples, the EMS apparatus and any method described herein may be used in combination with, including before, during and/or after, performing physical exercise and the amount of weight loss (e.g., decrease in BMI, PBF, weight, etc.) can be higher than physical activity without the EMS apparatus. In some examples, the combined use of any EMS apparatus and method described herein may increase a rate of weight loss equal to or greater than 1%, 2%, 3%, 4%, 5%, 10%, 15%, 20%, 30%, 40%, 50%, 60%, 70%, 80%, 90%, 100% or more, including any value therebetween, compared to physical activity and/or no activity without the use of an EMS apparatus.. In some examples, the combined use of any EMS apparatus and method described herein may increase a quantity of weight loss equal to or greater than 1%, 2%, 3%, 4%, 5%, 10%, 15%, 20%, 30%, 40%, 50%, 60%, 70%, 80%, 90%, 100% or more, including any percentage therebetween, compared to physical activity and/or no activity without the use of an EMS apparatus.

In some examples, a user may be an aged user. For example, aging may be considered a disease or condition associated with physiological, biological, molecular, or other changes associated with their ability to lose weight. Accordingly, any EMS apparatus or method described herein may increase a rate and/or quantity of weight loss compared to physical activity alone, or no activity in a user greater than or equal to the age of 5, 10, 15, 20, 25, 30, 35, 40, 45, 50, 55, 60, 65, 70, 75, 80, 85, 90, 100 or more, or any age therebetween. For example, a user over the age of 20 may engage an EMS apparatus as described herein and receive electrical stimulation in combination with physical exercise resulting in an increased rate or weight loss, increased quantity of weight loss, or a combination thereof, compared to physical exercise alone.

In some examples, a user may have one or more naturally occurring, environmentally induced, or a combination thereof, molecular aberrations associated with a metabolic deficiency. The user may engage an EMS apparatus described herein and receive electrical stimulation according to a stimulation protocol (e.g., including user-specific data) that may have one or more stimulation patterns, frequencies, patterns, etc. causing an increased rate of weight loss or quantity of weight loss compare to physical exercise or no physical exercise alone. For example, the user may have a germline or somatic mutation in a protein associated with hormone dysregulation, metabolic dysfunction, cellular activity, etc.; and the user may receive electrical stimulation according to a user-specific stimulation protocol (e.g., stimulation protocol) for an increased rate of weight loss and/or an increase quantity of weight loss compared to physical exercise without an EMS apparatus.

In some examples, the user EMS apparatus may acquire, determine, and/or receive information related to the type of fat or composition of fat (e.g., adipose tissue) associated with the user. For example, the type of fat may be brown fat, white fat, beige fat, visceral fat, subcutaneous fat, etc. or a combination thereof. In some examples, the EMS apparatus may be configured to distinguish between the different types of fat. For example, one or more sensors of the EMS apparatus may be configured to determine a quantity or concentration of one or more types of fat within the user. In some examples, the EMS apparatus may communicate with one or more remote networks (e.g., remote devices) to determine the quantity of one or more fat types. In some examples, based on the determined type of fat (e.g., in an anatomic region) the stimulation protocol may be established with one or more factors (e.g., intensity, pattern, frequency, duration, location, etc.) to optimize application of electrical stimulation and increase weight loss. In some examples, the type of fat may be associated with different cellular mechanisms such as different cellular metabolic processes in biological tissues (e.g., muscle tissue, fat tissue, etc.).

In some examples, the user may be diagnosed with a disease or condition (e.g., a neurological disorder). In some examples, the user may be at risk of developing a disease or condition. In some examples, the user may have a disease or condition and not exhibit any sign or symptom of the disease or condition. In some examples, the user may exhibit a sign or symptom of a disease or condition without being diagnosed with the disease or condition.

In some examples, a user is at risk of a disease or condition based on the user's family history, age, sex, lifestyle, habits, comorbidity, genetic mutations, acquired molecular aberrations etc.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

In general, any of the methods and apparatuses described herein may be used for weight loss. The methods and apparatuses may be used alone or in combination with a physical exercise activity. For example, EMS may be used as a weight loss tool for a range of patients alone or with other conventional physical activities. For example EMS may be engaged (e.g., worn) by a user before physical exercise, during physical exercise, after physical exercise or a combination thereof for increasing the amount of work and energy expended by one or more muscle groups, for support weight loss, for improved circulation for increasing and/or maintenance joint range of motion, for an increase in cardiovascular function (e.g., via simultaneous activity of large muscle groups), for maintenance of bone density; and/or for restorative therapy.

In some examples, any of the methods and apparatuses described herein may be used to continue muscle activity associated with a physical exercise during a time when the user is not performing a physical exercise. For example, a user may engage the EMS apparatus prior to beginning a physical exercise and the EMS apparatus may supply electrical stimulation via the one or more electrodes, as described herein (e.g., according to a simulation protocol) prior to physical exercise. In some examples, electrical stimulation prior to physical exercise may be configured to prepare one or more muscle groups for a physical exercise to follow. The user may then begin a physical activity and the EMS apparatus may be configured to determine the user is performing a physical exercise. In some examples, based on the EMS apparatus determination of the user performing a physical exercise, the EMS apparatus may supply electrical stimulation while the exercise is being performed, during a period of time no exercise is being performed, or after.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term “computer-readable medium,” as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being “on” another feature or element, it can be directly on the other feature or element or intervening features and/or elements may also be present. In contrast, when a feature or element is referred to as being “directly on” another feature or element, there are no intervening features or elements present. It will also be understood that, when a feature or element is referred to as being “connected”, “attached” or “coupled” to another feature or element, it can be directly connected, attached or coupled to the other feature or element or intervening features or elements may be present. In contrast, when a feature or element is referred to as being “directly connected”, “directly attached” or “directly coupled” to another feature or element, there are no intervening features or elements present. Although described or shown with respect to one embodiment, the features and elements so described or shown can apply to other embodiments. It will also be appreciated by those of skill in the art that references to a structure or feature that is disposed “adjacent” another feature may have portions that overlap or underlie the adjacent feature.

Terminology used herein is for the purpose of describing particular embodiments only and is not intended to be limiting of the invention. For example, as used herein, the singular forms “a”, “an” and “the” are intended to include the plural forms as well, unless the context clearly indicates otherwise. It will be further understood that the terms “comprises” and/or “comprising,” when used in this specification, specify the presence of stated features, steps, operations, elements, and/or components, but do not preclude the presence or addition of one or more other features, steps, operations, elements, components, and/or groups thereof. As used herein, the term “and/or” includes any and all combinations of one or more of the associated listed items and may be abbreviated as “/”.

Spatially relative terms, such as “under”, “below”, “lower”, “over”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as “under” or “beneath” other elements or features would then be oriented “over” the other elements or features. Thus, the exemplary term “under” can encompass both an orientation of over and under. The device may be otherwise oriented (rotated 90 degrees or at other orientations) and the spatially relative descriptors used herein interpreted accordingly. Similarly, the terms “upwardly”, “downwardly”, “vertical”, “horizontal” and the like are used herein for the purpose of explanation only unless specifically indicated otherwise.

Although the terms “first” and “second” may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as “consisting of” or alternatively “consisting essentially of” the various components, steps, sub-components or sub-steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for increasing weight-loss due to exercise, the method comprising:

positioning an electrical muscle stimulation (EMS) suit apparatus on a patient, the EMS suit apparatus having one or more electrodes locatable in direct contact with the patient's skin;

sensing patient biometric data before the patient exercises using one or more sensors on the EMS suit apparatus and establishing a threshold based on the patient biometric data;

supplying stimulation to one or more target muscle groups, via EMS power from the one or more electrodes;

sensing a patient movement data from the one or more sensors while and/or after the stimulation is supplied while the patient is exercising;

dynamically adjusting the stimulation or terminating stimulation based on a comparison between the patient movement data and the threshold; and providing, to the patient, a confirmation of use of the one or more target muscle group based on the patient movement data.

2. The method of claim 1, wherein the one or more target muscle groups includes quadriceps, hamstrings, glutes, abdominals, chest, lower back, mid back, upper back (trapezius), biceps and triceps, calves, or a combination thereof.

3. The method of claim 1, wherein sensing patient biometric data further comprises receiving additional patient biometric data from one or more sensors in operable communication with the EMS suit apparatus.

4. The method of claim 1, further comprising the patient performing a first exercise.

5. The method of claim 4, wherein stimulation is supplied to the one or more target muscle groups prior to the first exercise.

6. The method of claim 4, wherein stimulation is supplied to the one or more target muscle groups after the first exercise.

7. The method of claim 4, wherein stimulation is supplied to the one or more target muscle groups during the first exercise.

8. The method of claim 4, further comprising the patient performing a subsequent exercise.

9. The method of claim 8, further comprising verifying, by a controller, performance of the first exercise.

10. The method of claim 8, wherein stimulation is supplied to the one or more target muscle groups prior to the subsequent exercise.

11. The method of claim 8, wherein stimulation is supplied to the one or more target muscle groups after the subsequent exercise.

12. The method of claim 8, wherein stimulation is supplied to the one or more target muscle groups during the subsequent exercise.

13. The method of claim 1, wherein the EMS power is based on an initial baseline level, a user provided input, a power level provided by clinician, or a combination thereof.

14. The method of claim 1, wherein the confirmation includes a visual indication, a verbal confirmation, a haptic indication, or a combination thereof.

15. The method of claim 1, further comprising establishing, by a controller, a stimulation regime based on patient biometric data.

16. The method of claim 15, wherein the stimulation regime is adjustable by the controller.

17. The method of claim 1, further comprising:

prior to providing EMS power to the one or more electrodes, determining movement of the one or more target muscle groups; and providing EMS power in response to determining movement of the one or more target muscle groups.

18. The method of claim 1, further comprising:

determining a weight loss of the patient with respect to a predetermined time period; and providing, to the patient, exercises to perform for the one or more target muscle groups, wherein the exercises are based on the determined weight loss of the patient.

19. The method of claim 1, wherein stimulation is supplied to the one or more target muscle groups before an exercise, during an exercise, after an exercise, or a combination thereof.

20. A method for increasing weight-loss due to exercise, the method comprising:

positioning an electrical muscle stimulation (EMS) suit apparatus on a patient, the EMS suit apparatus having one or more electrodes locatable in direct contact with the patient's skin;

sensing patient biometric data before the patient exercises using one or more accelerometers on the EMS suit and apparatus establishing a threshold based on the patient biometric data;

supplying stimulation to one or more target muscle groups, via EMS power from the one or more electrodes;

sensing a patient movement data from the one or more accelerometers while and/or after the stimulation is supplied while the patient is exercising;

dynamically adjusting the stimulation or terminating stimulation based on a comparison between the patient movement data and the threshold; and providing, to the patient, a confirmation of use of the one or more target muscle groups based on the patient movement data.

* * * * *